US009018321B2

(12) United States Patent
Amano et al.

(10) Patent No.: US 9,018,321 B2
(45) Date of Patent: Apr. 28, 2015

(54) RESIN COMPOSITION

(75) Inventors: Hiroshi Amano, Kawasaki (JP); Shigeru Kawahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 124 days.

(21) Appl. No.: 12/180,115

(22) Filed: Jul. 25, 2008

(65) Prior Publication Data
US 2009/0030158 A1 Jan. 29, 2009

Related U.S. Application Data

(60) Provisional application No. 60/952,384, filed on Jul. 27, 2007.

(30) Foreign Application Priority Data

Jul. 26, 2007 (JP) ................. 2007/195141

(51) Int. Cl.
C08F 283/10 (2006.01)
C08G 75/00 (2006.01)
C08L 81/00 (2006.01)
C07F 9/54 (2006.01)
B01J 31/02 (2006.01)
C07D 233/58 (2006.01)
C08L 63/00 (2006.01)

(52) U.S. Cl.
CPC ........... *C07F 9/5407* (2013.01); *B01J 31/0277* (2013.01); *C07D 233/58* (2013.01); *C08L 63/00* (2013.01); *C08L 81/00* (2013.01)

(58) Field of Classification Search
CPC .................................................. C08L 63/00
USPC .................. 525/403, 523, 535; 548/335.1
See application file for complete search history.

(56) References Cited

U.S. PATENT DOCUMENTS

| 3,635,894 | A |   | 1/1972  | Dowbenko et al. |
|-----------|---|---|---------|-----------------|
| 4,413,137 | A | * | 11/1983 | Renga et al. ................... 549/518 |
| 4,594,291 | A |   | 6/1986  | Bertram et al. |
| 4,725,652 | A |   | 2/1988  | Bertram et al. |
| 4,925,901 | A |   | 5/1990  | Bertram et al. |
| 4,946,817 | A |   | 8/1990  | Bertram et al. |
| 5,134,239 | A |   | 7/1992  | Bertram et al. |
| 5,212,261 | A | * | 5/1993  | Stierman ........................ 525/506 |
| 5,407,977 | A | * | 4/1995  | Everett et al. ................. 523/429 |
| 5,430,112 | A |   | 7/1995  | Sakata et al. |
| 5,503,937 | A |   | 4/1996  | Bertram et al. |
| 5,763,507 | A | * | 6/1998  | Moriga et al. ................. 523/424 |
| 6,492,483 | B1| * | 12/2002 | Li et al. ............................ 528/89 |
| 6,596,130 | B2|   | 7/2003  | Westman |
| 6,613,839 | B1|   | 9/2003  | Gan et al. |
| 7,507,779 | B2|   | 3/2009  | Nagano et al. |
| 2002/0103323 | A1| * | 8/2002 | Westmeyer et al. ............ 528/12 |
| 2004/0086720 | A1|   | 5/2004 | Gan et al. |
| 2006/0052493 | A1|   | 3/2006 | Nagano et al. |
| 2006/0139426 | A1|   | 6/2006 | Doi |
| 2006/0229400 | A1| * | 10/2006 | Fletcher ........................ 524/430 |
| 2007/0021582 | A1|   | 1/2007 | Amano et al. |
| 2008/0265201 | A1|   | 10/2008 | Spyrou et al. |
| 2009/0035580 | A1|   | 2/2009 | Chino et al. |
| 2009/0234080 | A1| * | 9/2009 | Goh .............................. 525/523 |
| 2010/0166971 | A1|   | 7/2010 | Wittenbecher et al. |

FOREIGN PATENT DOCUMENTS

| CN | 1687085 A | 10/2005 |
| CN | 1743391 A | 3/2006 |
| EP | 0 458 502 A2 | 11/1991 |
| JP | 61-293216 | 12/1986 |
| JP | 61-293216 A | 12/1986 |
| JP | 6-211969 | 8/1994 |
| JP | 11-158251 A | 6/1996 |
| JP | 2001-508828 A | 7/2001 |
| JP | 2003-500460 A | 1/2003 |
| JP | 2004-217931 A | 8/2004 |
| JP | 2004-269414 A | 9/2004 |
| JP | 2005-325178 A | 11/2005 |
| JP | 2006-188551 A | 7/2006 |
| JP | 2007-9124 A | 1/2007 |
| JP | 2007-70370 | 3/2007 |
| JP | 2007-70399 A | 3/2007 |
| JP | 2008/163272 A | 7/2008 |
| JP | 2008-191544 A | 8/2008 |
| JP | 2008-285414 A | 11/2008 |
| JP | 2010/530908 | 9/2010 |
| WO | WO 86/00627 A1 | 1/1986 |
| WO | WO 2006/090819 A1 | 8/2006 |
| WO | WO 2007/018239 A1 | 2/2007 |

(Continued)

OTHER PUBLICATIONS

U.S. Appl. No. 60/952,384, filed Jul. 27, 2007, Amano, et al.
Kowalczyk K. et al., "Ionic liquids as convenient latent hardeners of eoxy resins", Polimery 2003, 48, nr 11-12, p. 833-835.
ChemFiles Ion Ekitai, vol. 2, vol. 6, No. 9, Shiguma Arudoricchi Japan Kabushiki Kaisha, 2006, 16 pp. (w/English Translation).
International Search Report mailed Feb. 18, 2010 in PCT/JP2008/063852, filed Jul. 25, 2008.
Extended Search Report issued Jan. 21, 2014, in European patent application No. 13192563.8.
"Performance of bismuth vanadates in polyester/trimellictic acid triglycidylester powder" retrieved from the Internet (http://www.wwrchk.com/admin/upload/manufacturers/10_6618B_original.pdf), Feb. 2013, XP055096088.
Trihexyltetradecylphosphonium decanoate retrieved from the Internet (http://www.sigmaaldrich.com/catalog/product/aldrich/50826?lang=en ion=NL#), Jan. 13, 2014, XP055096097.

(Continued)

*Primary Examiner* — Megan McCulley
(74) *Attorney, Agent, or Firm* — Oblon, McClelland, Maier & Neustadt, L.L.P.

(57) ABSTRACT

Resin compositions which contain a compound having at least two epoxy and/or thiirane groups in the molecule (ingredient (1)) and a specific ionic liquid (ingredient (2)), as combined, are practicable resin compositions which comprise constitutive elements of readily available materials and have well-balanced suitable curing capability and storage stability. Preferably, the ionic liquid (ingredient (2)) comprises a combination of an ammonium cation or phosphonium cation and a carboxylate anion.

37 Claims, 1 Drawing Sheet

(56) References Cited

FOREIGN PATENT DOCUMENTS

| WO | WO 2007037024 | * | 4/2007 |
| WO | WO 2008/138855 | | 11/2008 |
| WO | WO 2008/152003 A1 | | 12/2008 |

OTHER PUBLICATIONS

Chinese Office Action issued Sep. 14, 2011 in patent application No. 200880021213.5 (with English Translation).

H.Q. Pham, et al., "Epoxy Resins", Encyclopedia of Polymer Science and Technology, vol. 9, XP007920796, Jan. 1, 2004, pp. 678-804.

* cited by examiner

RESIN COMPOSITION

CROSS REFERENCES TO RELATED APPLICATIONS

This application claims priority to U.S. Provisional Patent Application No. 60/952,384, filed on Jul. 27, 2007, and Japanese Patent Application No. 195141/2007, filed on Jul. 26, 2007, both of which are incorporated herein by reference in their entireties.

BACKGROUND OF THE INVENTION

1. Field of the Invention

The present invention relates to resin compositions which have good curing capability and storage stability. The invention further relates to cured products prepared by curing such a composition. The present invention also relates to novel ionic liquids which are useful as curing accelerators and/or curing agents.

2. Discussion of the Background

An epoxy resin composition is a general-purpose synthetic resin widely utilized in various fields of adhesives, sealants, coating agents, etc. A "two-component" epoxy resin composition was once the mainstream, but because of its troublesome and inconvenience in that the main ingredient and the curing agent must be mixed just before use, a "one-component" epoxy resin composition has been developed.

JP-A 06-211969 discloses a most typical "one-component" epoxy resin composition that comprises a dicyandiamide, a dihydrazide compound or an amine adduct compound as a "solid dispersion-type curing accelerator". These have a special structure, and could not always be said to be easily available.

On the other hand, *Polimery*, vol. 48, pp. 833-835 (2003) reports that a specific ionic liquid, 1-butyl-3-methylimidazolium tetrafluoroborate is usable as a curing agent for epoxy resin. However, the curing temperature is at least 190° C. and is high, and even when it is added in an amount of from 1 to 5 parts by weight relative to 100 parts by weight of epoxy resin, it needs a long period of time of from 6.5 to 7 hours; and therefore, it is not on a practicable level at all.

Thus, conventional curing agents and curing accelerators for use in epoxy resin compositions have various problems as described above, and could not always be said as practicable resin compositions of excellent operability and reliability.

SUMMARY OF THE INVENTION

Accordingly, it is one object of the present invention to provide novel resin compositions.

It is another object of the present invention to provide novel resin compositions which comprise constitutive elements of readily available materials and have well-balanced suitable curing capability and storage stability.

It is another object of the present invention to provide novel cured products obtained by curing such a resin composition.

It is another object of the present invention to provide novel ionic liquids.

It is another object of the present invention to provide novel ionic liquids which are useful as curing accelerators.

These and other objects, which will become apparent during the following detailed description, have been achieved by the inventors' discovery that a combination of at least one compound having at least two epoxy and/or thiirane groups in the molecule (ingredient (1)) and at least one ionic liquid (ingredient (2)) can solve the above-described problems.

Specifically, the invention includes the following embodiments:

(1) A resin composition comprising:
(a) at least one compound (ingredient (1)) selected from the group consisting of:
(a1) a compound which contains at least two epoxy groups in the molecule;
(a2) a compound which contains at least two thiirane groups in the molecule; and
(a3) a compound which contains at least one epoxy group and at least one thiirane group in the molecule; and
(b) at least one ionic liquid (ingredient (2)).

(2) The resin composition of (1), wherein the at least one ionic liquid (ingredient (2)) comprises (b1) at least one ammonium cation or at least one phosphonium cation and (b2) at least one carboxylate anion.

(3) The resin composition of (2), wherein the carboxylate anion is at least one anion selected from a 2-pyrrolidone-5-carboxylate ion, a formate ion, a lactate ion, a tartrate ion, a hippurate ion, an N-methylhippurate ion, an N-benzoylalaninate ion, an N-acetylphenylalaninate ion and an N-acetylglycinate ion.

(4) The resin composition of any of (1) to (3), which further comprises:
(c) at least one polythiol compound having at least two thiol groups in the molecule (ingredient (3)).

(5) The resin composition of any of (1) to (4), which further comprises:
(d) at least one compound having Lewis acidity (ingredient (4)).

(6) The resin composition of any of (1) to (3) which further comprises:
(e) at least one acid anhydride (ingredient (5)).

(7) A fine chemical product comprising the resin composition of any of (1) to (6).

(8) A cured product, which is obtained by curing a resin composition of (1).

(9) An ionic liquid comprising:
(a) at least one cation selected from a group consisting of an imidazolium ion and a tetraalkylphosphonium ion; and
(b) at least one anion selected from a group consisting of a formate ion, a lactate ion, a tartrate ion, a hippurate ion, an N-methylhippurate ion, an N-benzoylalaninate ion, an N-acetylphenylalaninate ion, a 2-pyrrolidone-5-carboxylate ion and an N-acetylglycinate ion.

(10) An ionic liquid of any of 1-butyl-3-methylimidazolium lactate, tetrabutylphosphonium 2-pyrrolidone-5-carboxylate, tetrabutylphosphonium formate, tetrabutylphosphonium lactate, tetrabutylphosphonium hippurate, tetrabutylphosphonium benzoyl-DL-alaninate, tetrabutylphosphonium N-acetylglycinate, 1-ethyl-3-methylimidazolium lactate, 1-ethyl-3-methylimidazolium formate, 1-ethyl-3-methylimidazolium hippurate, bis(1-ethyl-3-methylimidazolium) tartrate, and 1-ethyl-3-methylimidazolium N-acetylglycinate.

(11) A curing accelerator comprising the ionic liquid of any of (8) or (9).

According to the present invention, a practicable resin composition can be obtained, which comprises constitutive elements of easily available materials and which has well-balanced suitable curing capability and storage stability. In particular, when an ambient temperature ionic liquid is used, the invention may provide a complete liquid, one-component resin composition of good operability favorable for narrow adhesion and impregnation adhesion.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows graphically the results of differential scanning calorimetry (DSC) of Examples 47 to 51 (with ionic liquids R, S, T, U and V).

DETAILED DESCRIPTION OF THE PREFERRED EMBODIMENTS

Figure 1:
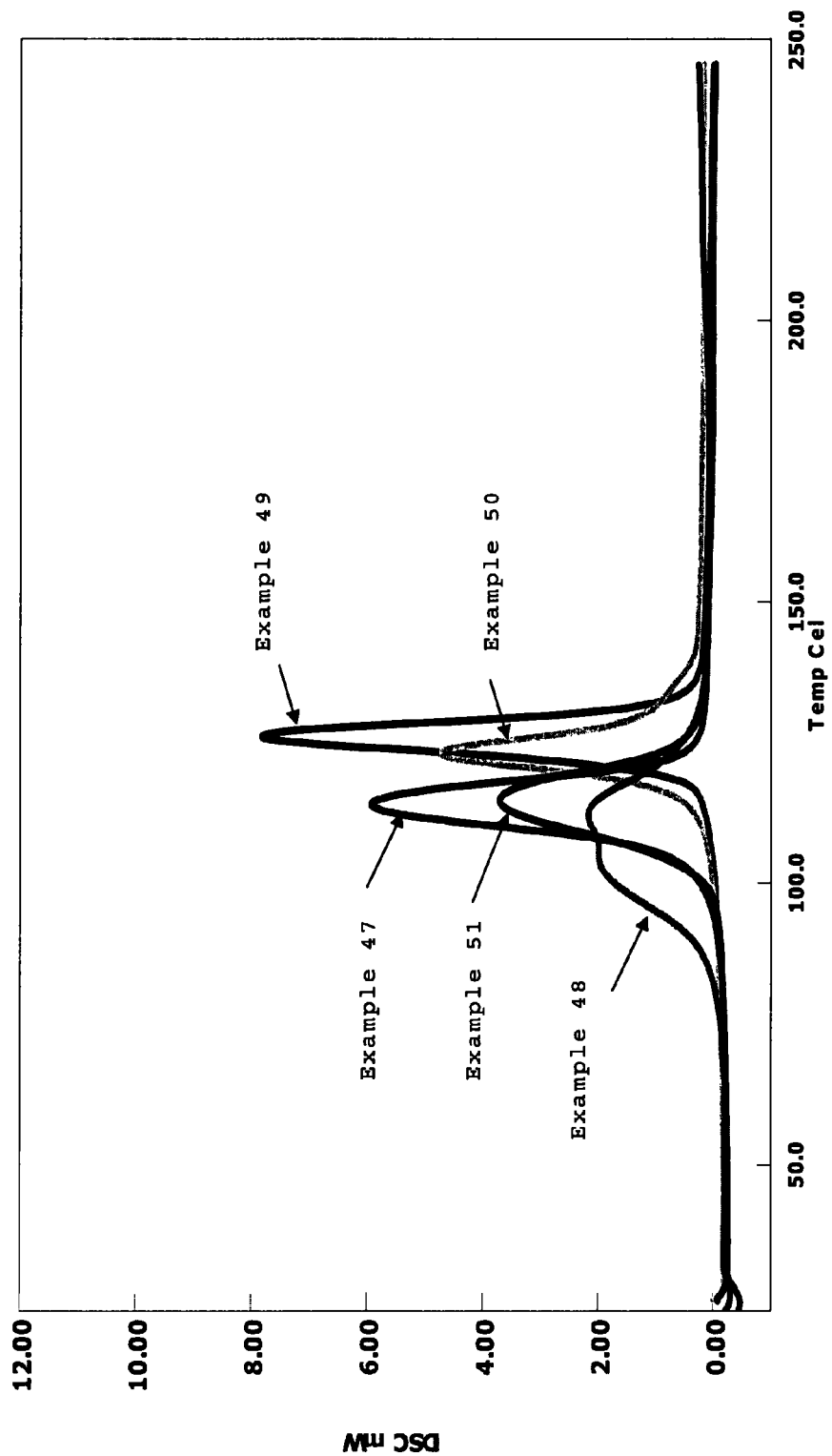

In the context of the present invention, the term "resin" means a polymer precursor compound capable of giving a three-dimensional network structure in the presence of a suitable reagent, and for example, it includes epoxy resin and others described below. In this description, the polymer precursor compound and a composition comprising it are referred to as "resin" and "resin composition", respectively; and their polymerized and cured products are referred to as "cured products". The term "ionic liquid" generally means "a salt comprising an anion and a cation and capable of melting at a temperature falling within a range not higher than about 100° C."; but in this description, this term means "a salt comprising an anion and a cation and capable of melting at a temperature falling within a range not higher than the curing temperature", preferably "a molten salt at an ambient temperature comprising an anion and a cation".

The resin composition of the invention is characterized by comprising a compound having at least two epoxy and/or thiirane groups in the molecule, and a specific ionic liquid; therefore providing a practicable resin composition that comprises constitutive elements of easily available materials and has well-balanced suitable curing capability and storage stability. Further using the ingredients described below, the resin composition may be designed to have a desired curing time and storage stability.

Ingredient (1).

The ingredient (1) for use in the resin composition of the invention is a compound having at least two epoxy and/or thiirane groups in the molecule, and is any of (A) a compound having at least two thiirane groups in the molecule, (B) a compound having both at least one thiirane group and at least one epoxy group in the molecule, and (C) a compound having at least two epoxy groups in the molecule. One or more those compounds (A) to (C) may be used singly or as combined; but preferably, the compound (C) is used singly as it enhances the strength of the cured product.

From the viewpoint of improving the storage stability/gelling time selectivity, the proportion (% by weight) of the thiirane group-containing compound in the ingredient (1) is preferably from 60 to 100% by weight, more preferably from 80 to 100% by weight. In this context, the term "thiirane group-containing compound in the ingredient (1)" means the sum of the weight of (A) and the thiirane partial weight of (B), referred to as (B*), where the thiirane partial weight (B*) is calculated by the following formula:

thiirane partial weight (B*)=(weight of (B))×(the moles of thiirane groups in (B))÷(moles of thiirane groups in (B)+the moles of epoxy groups in (B)).

In other words, the thiirane partial weight (B*) is calculated by multiplying the weight of (B) by the number of moles of thiirane groups in the molecule, and then dividing that number by the sum of the number of moles of thiirane groups and the number of moles of epoxy groups in the molecule, to arrive at the thiirane partial weight (B*). The weight of the (A) and the thiirane partial weight (B*) are then added together to arrive at the weight of the thiirane-containing compound.

The thiirane group-containing compound in the invention may be produced in various methods. For example, the methods include thermal dehydration of 2-hydroxymercaptan, processing of 1,2-chlorothiol with a weak alkaline solution, and processing of an ethylenic unsaturated ether with sulfur or a compound such as polysulfide dialkyl.

Already known is a method of obtaining a thiirane group-containing compound, starting from an epoxy compound and substituting all or a part of the oxygen atom of the epoxy group with a sulfur atom. The compound of the type may be referred to as episulfide or episulfide resin. Its examples include a method of using an epoxy compound and a thiocyanic acid salt as described in *J. Polym. Sci. Polym. Phys.*, vol. 17, p. 329 (1979); a method of using an epoxy compound and a thiourea as described in *J. Org. Chem.*, vol. 26, p. 3467 (1961); and methods described in JP-A 2000-351829 and 2001-342253, to which, however, the invention should not be limited.

Specific examples of the compound (A) having at least two thiirane groups in the molecule, described in detail in the above are, for example, 2,2-bis(4-(2,3-epithiopropoxy)phenyl)propane, bis(4-(2,3-epithiopropoxy)phenyl)methane, 1,6-di(2,3-epithiopropoxy)naphthalene, 1,1,1-tris-(4-(2,3-epithiopropoxy)phenyl)ethane, 2,2-bis(4-(2,3-epithiopropoxy)cyclohexyl)propane, bis(4-(2,3-epithiopropoxy)cyclohexyl)methane, 1,1,1-tris-(4-(2,3-epithiopropoxy)cyclohexyl)ethane, 1,5-pentanediol (2,3-epithiocyclohexyl)ether and 1,6-hexanediol di(3,4-epithiooctyl)ether, to which, however, the invention should not be limited.

The compound (B) having both a thiirane group and an epoxy group in one molecule in the invention can be obtained as follows: In a process of starting from an epoxy compound and substituting the oxygen atom of the epoxy group with a sulfur atom to produce an episulfide resin, the amount of the episulfidization reagent to be used or the reaction condition is controlled. A partial episulfide compound obtained through separation in various purification methods can be mixed with a complete episulfide compound for use herein.

A more preferred thiirane group-containing compound for use in the invention is a thiirane group-containing compound produced by substituting all or a part of the oxygen atom of the epoxy group of a hydrogenated bisphenol-epoxy resin that is prepared through hydrogenation (for hydrogen addition) of the carbon-carbon unsaturated bond of the aromatic ring of a bisphenol skeleton-having epoxy compound, with a sulfur atom, as in JP-A 2000-351829; especially a hydrogenated bisphenol A skeleton-having thiirane group-containing compound. The composition comprising the compound is especially excellent in curability, operability and storage stability.

The compound (C) having at least two epoxy groups in the molecule for use in the invention may be any one having at least two epoxy groups per molecule on average. For example, it includes polyphenols such as bisphenol A, bisphenol F, bisphenol AD, catechol, resorcinol; polyglycidyl ethers prepared by reacting a polyalcohol such as glycerin or polyethylene glycol, and epichlorohydrin; glycidyl ether esters prepared by reacting a hydroxycarboxylic acid such as p-hydroxybenzoic acid or β-hydroxynaphthoic acid, and epichlorohydrin; polyglycidyl esters prepared by reacting a polycarboxylic acid such as phthalic acid or terephthalic acid, and epichlorohydrin; and further epoxidated phenol-novolak resins, epoxydated cresol-novolak resins, epoxidated polyolefins, cycloaliphatic epoxy resins and other urethane-modified epoxy resins, to which, however, the invention should not be limited.

Commercial epoxy resin products are, for example, Japan Epoxy Resin's Epikote 828, 1001, 801, 806, 807, 152, 604, 630, 871, YX8000, YX8034, YX4000, Cardula E1 OP; Dai-Nippon Ink Industry's Epiclon 830, 835LV, HP4032D, 703, 720, 726, HP820; Asahi Denka Kogyo's EP4100, EP4000, EP4080, EP4085, EP4088, EPU6, EPR4023, EPR1309, EP49-20; and Nagase ChemteX's Denacol EX411, EX314, EX201, EX212, EX252, EX 111, EX146, EX721, to which, however, the invention should not be limited. One or more of these may be used either singly or as combined.

The above-mentioned ingredients (A) to (C) may have any other functional group than the epoxy group and the thiirane group. For example, it includes a hydroxyl group, a vinyl group, an acetal group, an ester group, a carbonyl group, an amide group, an alkoxysilyl group.

Ingredient (2).

The ionic liquid of the ingredient (2) for use in the invention is a salt comprising an anion and a cation and meltable within a temperature range not higher than the curing temperature; and this acts both as a resin curing agent and as a curing accelerator. In the composition of the invention, it is desirable that the ingredient (2) uniformly dissolves in the ingredient (1), and from the viewpoint of readily preparing the composition, the melting point of the ingredient (2) is preferably lower than an ambient temperature.

The cation to constitute the ionic liquid includes ammonium cations such as an imidazolium ion, a piperidinium ion, a pyrrolidinium ion, a pyrazolium ion, a guanidinium ion, a pyridinium ion; phosphonium cations such as a tetrabutylphosphonium ion, a tributylhexylphosphonium ion; and sulfonium cations such as a triethylsulfonium ion.

The anion to constitute the ionic liquid includes halide anions such as a fluoride ion, a chloride ion, a bromide ion, an iodide ion; alkylsulfate anions such as a methanesulfonate ion; fluorine-containing compound anions such as a trifluoromethanesulfonate ion, a hexafluorophosphonate ion, a trifluorotris(pentafluoroethyl)phosphonate ion, a bis(trifluoromethanesulfonyl)imidate ion, a trifluoroacetate ion, a tetrafluoroborate ion; phenolic anions such as a phenol ion, a 2-methoxyphenol ion, a 2,6-di-tert-butylphenol ion; acidic amino acid ions such as an aspartate ion, a glutamate ion; neutral amino acid ions such as a glycinate ion, an alaninate ion, a phenylalaninate ion; N-acylamino acid ions represented by the following general formula (1), such as an N-benzoylalaninate ion, an N-acetylphenylalaninate ion, an N-acetylglycinate ion; and carboxylate anions such as a formate ion, an acetate ion, a decanoate ion, a 2-pyrrolidone-5-carboxylate ion, an α-lipoate ion, a lactate ion, a tartrate ion, a hippurate ion, an N-methylhippurate ion, a benzoate ion.

Formula 1:

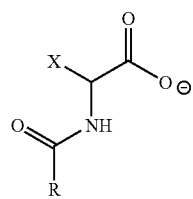

(1)

wherein R—CO— represents an acyl group derived from a linear or branched chain fatty acid having from 1 to 5 carbon atoms, or a substituted or unsubstituted benzoyl group; —NH—CHX—CO$_2^-$ represents an acidic amino acid ion such as an aspartate or glutamate ion, or a neutral amino acid ion such as a glycinate, alaninate or phenylalaninate ion.

First described is the ionic liquid suitable to the resin composition comprising the ingredient (1), the ingredient (2), and the ingredient (3), and/or the ingredient (4). In this case, the ionic liquid serves as a curing accelerator.

The cation that constitutes the ionic liquid suitable to this application is preferably an ammonium cation and a phosphonium cation from the viewpoint of the good balance of the curability and the storage stability, and more preferably an imidazolium ion, a piperidinium ion, a pyrrolidinium ion, a pyridinium ion, a phosphonium ion, even more preferably an imidazolium ion, a phosphonium ion.

The anion that constitutes the ionic liquid suitable to this application is preferably a fluorine-containing compound anion, a phenolic anion, an N-acylamino acid ion represented by the general formula (1) and a carboxylate anion, from the viewpoint of the good balance of the curability and the storage stability, and more preferably a hexafluorophosphate ion, a bis(trifluoromethanesulfonyl)imidate ion, a 2-methoxyphenol ion, a 2,6-di-tert-butylphenol ion, an acetate ion, a decanoate ion, a 2-pyrrolidone-5-carboxylate ion, a formate ion, an α-lipoate ion, a lactate ion, a tartrate ion, a hippurate ion, an N-methylhippurate ion, an N-benzoylalaninate ion, an N-acetylphenylalaninate ion and an N-acetylglycinate ion, even more preferably a 2,6-di-tert-butylphenol ion, a 2-pyrrolidone-5-carboxylate ion, an acetate ion, a decanoate ion, a formate ion, an X-lipoate ion, a lactate ion, a hippurate ion, an N-methylhippurate ion, an N-benzoylalaninate ion, an N-acetylphenylalaninate ion, a benzoate ion, a glycinate ion and an N-acetylglycinate ion, still more preferably a 2-pyrrolidone-5-carboxylate ion, an acetate ion, a decanoate ion, a formate ion, a lactate ion, a 2,6-di-tert-butylphenol ion, a hippurate ion, an N-methylhippurate ion, an N-benzoylalaninate ion, a benzoate ion and an N-acetylglycinate ion, especially preferably 2-pyrrolidone-5-carboxylate ion, an acetate ion, a decanoate ion, a formate ion, a lactate ion, an N-methylhippurate ion, a benzoate ion and an N-acetylglycinate ion, and still especially preferably a 2-pyrrolidone-5-carboxylate ion, a formate ion and an N-acetylglycinate ion.

Concretely, from the viewpoint of the good balance of the curability and the storage stability, the ionic liquid is preferably 1-butyl-3-methylimidazolium hexafluorophosphate, 1-butyl-3-methylimidazolium lactate, N-methyl-N-propylpiperidinium bis(trifluoromethanesulfonyl)imidate, N-methyl-N-propylpyrrolidinium bis(trifluoromethanesulfonyl)imidate, N-hexylpyridinium bis(trifluoromethylsulfonyl)imidate, tetrabutylphosphonium 2-pyrrolidone-5-carboxylate, tetrabutylphosphonium acetate, tetrabutylphosphonium decanoate, tetrabutylphosphonium trifluoroacetate, tetrabutylphosphonium α-lipoate, tetrabutylphosphonium formate, tetrabutylphosphonium lactate, bis(tetrabutylphosphonium) tartrate, tetrabutylphosphonium hippurate, tetrabutylphosphonium N-methylhippurate, tetrabutylphosphonium benzoyl-DL-alaninate, tetrabutylphosphonium N-acetylphenylalaninate, tetrabutylphosphonium methanesulfonate, tetrabutylphosphonium 2,6-di-tert-butylphenol, tetrabutylphosphonium benzoate, monotetrabutylphosphonium L-aspartate, tetrabutylphosphonium glycinate, tetrabutylphosphonium N-acetylglycinate, 1-ethyl-3-methylimidazolium acetate, 1-ethyl-1-methylpiperidinium 2-pyrrolidone-5-carboxylate, 1-ethyl-3-methylimidazolium formate; more preferably 1-butyl-3-methylimidazolium lactate, tetrabutylphosphonium 2-pyrrolidone-5-carboxylate, tetrabutylphosphonium acetate, tetrabutylphosphonium decanoate, tetrabutylphosphonium α-lipoate, tetrabutylphosphonium formate, tetrabutylphosphonium lactate, bis(tetrabutylphosphonium) tartrate, tetrabutylphosphonium hippurate, tetrabutylphosphonium N-methylhippurate, tetrabutylphosphonium benzoyl-DL-alaninate, tetrabutylphosphonium N-acetylphenylalaninate, tetrabutylphosphonium 2,6-di-tert-butylphenol, tetrabutylphosphonium benzoate, monotetrabutylphosphonium L-aspartate, tetrabutylphosphonium glycinate, tetrabutylphosphonium N-acetylglycinate, 1-ethyl-3-methylimidazolium acetate, 1-ethyl-1-methylpiperidinium 2-pyrrolidone-5-carboxylate, 1-ethyl-3-methylimidazolium formate; even more preferably 1-butyl-3-methylimidazolium lactate, tetrabutylphosphonium 2-pyrrolidone-5-carboxylate, tetrabutylphosphonium acetate, tetrabutylphosphonium decanoate, tetrabutylphosphonium α-lipoate, tetrabutylphosphonium formate, tetrabutylphosphonium lactate, bis(tetrabutylphosphonium) tartrate, tetrabutylphosphonium hippurate, tetrabutylphosphonium N-methylhippurate, tetrabutylphosphonium benzoyl-DL-alaninate, tetrabutylphosphonium N-acetylphenylalaninate, tetrabutylphosphonium 2,6-di-tert-butylphenol, tetrabutylphosphonium benzoate, monotetrabutylphosphonium L-aspartate, tetrabutylphosphonium glycinate, tetrabutylphosphonium N-acetylglycinate, 1-ethyl-3-methylimidazolium acetate, 1-ethyl-1-methylpiperidinium 2-pyrrolidone-5carboxylate, 1-ethyl-3-methylimidazolium formate; still more preferably tetrabutylphosphonium 2-pyrrolidone-5-carboxylate, tetrabutylphosphonium acetate, tetrabutylphosphonium decanoate, tetrabutylphosphonium formate, tetrabutylphosphonium lactate, tetrabutylphosphonium N-methylhippurate, tetrabutylphosphonium benzoate, tetrabutylphosphonium N-acetylglycinate, 1-ethyl-3-methylimidazolium acetate, 1-ethyl-1-methylpiperidinium 2-pyrrolidone-5-carboxylate, 1-ethyl-3-methyl imidazolium fommate.

Next described is the ionic liquid suitable for use in the resin composition comprising the ingredient (1) and the ingredient (2). In particular, when the ingredient (1) is the compound (C) having at least two epoxy groups in the molecule, the resin composition does not comprise a sulfur fraction, and therefore the stability of the resin itself, after cured, is extremely good. In this case, the ionic liquid serves as a curing agent.

The cation that constitutes the ionic liquid suitable to this application is preferably an ammonium cation and a phosphonium cation, more preferably an imidazolium ion and a phosphonium ion, even more preferably a phosphonium ion.

The anion that constitutes the ionic liquid suitable to this application is preferably a phenolic anion, an N-acylamino acid ion represented by the general formula (1), or a carboxylate anion; more preferably a 2,6-di-tert-butylphenol ion, an acetate ion, a decanoate ion, a 2-pyrrolidone-5-carboxylate ion, a formate ion, an α-lipoate ion, a lactate ion, a tartrate ion, a hippurate ion, an N-methylhippurate ion, an N-enzoylalaninate ion, an N-acetylphenylalaninate ion, an aspartate ion, a glycinate ion and an N-acetylglycinate ion; even more preferably a 2-pyrrolidone-5-carboxylate ion, a formate ion, an α-lipoate ion, a lactate ion, a tartrate ion, a hippurate ion, an N-methylhippurate ion, an N-benzoylalaninate ion, an N-acetylphenylalaninate ion, 2,6-di-tert-butylphenol ion and an N-acetylglycinate ion; still more preferably a 2-pyrrolidone-5-carboxylate ion, a formate ion, a lactate ion, a tartrate ion, a hippurate ion, an N-methylhippurate ion, an N-benzoylalaninate ion, an N-acetylphenylalaninate ion and an N-acetylglycinate ion; further more preferably a 2-pyrrolidone-5-carboxylate ion, a formate ion, a lactate ion, an N-benzoylalaninate ion and an N-acetylglycinate ion; especially preferably a 2-pyrrolidone-5-carboxylate ion and a formate ion.

Concretely, the ionic liquid suitable to this application is preferably 1-butyl-3-methylimidazolium lactate, tetrabutylphosphonium 2-pyrrolidone-5-carboxylate, tetrabutylphosphonium acetate, tetrabutylphosphonium decanoate, tetrabutylphosphonium trifluoroacetate, tetrabutylphosphonium α-lipoate, tetrabutylphosphonium formate, tetrabutylphosphonium lactate, bis(tetrabutylphosphonium) tartrate, tetrabutylphosphonium hippurate, tetrabutylphosphonium N-methylhippurate, tetrabutylphosphonium benzoyl-DL-alaninate, tetrabutylphosphonium N-acetylphenylalaninate, tetrabutylphosphonium 2,6-di-tert-butylphenol, monotetrabutylphosphonium L-aspartate, tetrabutylphosphonium glycinate, tetrabutylphosphonium N-acetylglycinate, 1-ethyl-3-methylimidazolium lactate, 1-ethyl-3-methylimidazolium formate, 1-ethyl-3-methylimidazolium hippurate, bis(1-ethyl-3-methylimidazolium) tartrate, 1-ethyl-3-methylimidazolium N-acetylglycinate; more preferably 1-butyl-3-methylimidazolium lactate, tetrabutylphosphonium 2-pyrrolidone-5-carboxylate, tetrabutylphosphonium formate, tetrabutylphosphonium lactate, bis(tetrabutylphosphonium) tartrate, tetrabutylphosphonium hippurate, tetrabutylphosphonium N-methylhippurate, tetrabutylphosphonium benzoyl-DL-alaninate, tetrabutylphosphonium N-acetylphenylalaninate, tetrabutylphosphonium N-acetylglycinate, 1-ethyl-3-methylimidazolium lactate, 1-ethyl-3-methylimidazolium formate, 1-ethyl-3-methylimidazolium hippurate, bis(1-ethyl-3-methylimidazolium) tartrate, 1-ethyl-3-methylimidazolium N-acetylglycinate; even more preferably 1-butyl-3-methylimidazolium lactate, tetrabutylphosphonium 2-pyrrolidone-5-carboxylate, tetrabutylphosphonium formate, tetrabutylphosphonium lactate, tetrabutylphosphonium hippurate, tetrabutylphosphonium benzoyl-DL-alaninate, tetrabutylphosphonium N-acetylglycinate, 1-ethyl-3-methylimidazolium lactate, 1-ethyl-3-methylimidazolium formate, 1-ethyl-3-methylimidazolium hippurate, bis(1-ethyl-3-methylimidazolium) tartrate, 1-ethyl-3-methylimidazolium N-acetylglycinate; still more preferably tetrabutylphosphonium 2-pyrrolidone-5-carboxylate, tetrabutylphosphonium form ate, tetrabutylphosphonium lactate, tetrabutylphosphonium benzoyl-DL-alaninate, tetrabutylphosphonium N-acetylglycinate, 1-ethyl-3-methylimidazolium formate, 1-ethyl-3-methylimidazolium N-acetylglycinate; further more preferably tetrabutylphosphonium 2-pyrrolidone-5-carboxylate, tetrabutylphosphonium formate, tetrabutylphosphonium N-acetylglycinate.

Next described is the ionic liquid suitable to the resin composition comprising the ingredient (1), the ingredient (2), and the ingredient (5). The resin composition of this type has somewhat poor storage stability but is suitable for applications that require short-time curing.

The cation that constitutes the ionic liquid suitable to this application is preferably an ammonium cation and a phosphonium cation, more preferably an imidazolium ion, a piperidinium ion, a pyrrolidinium ion, a pyridinium ion, a phosphonium ion, even more preferably a piperidinium ion, an imidazolium ion and a phosphonium ion, still more preferably a piperidinium ion, an imidazolium ion, and especially preferably a piperidinium ion.

The anion that constitutes the ionic liquid suitable to this application is preferably a fluorine-containing compound anion, a phenolic anion, an N-acylamino acid ion represented by the general formula (1), a carboxylate anion; more preferably a hexafluorophosphate ion, a bis(trifluoromethanesulfonyl)imidate ion, an acetate ion, a decanoate ion, a 2-pyrrolidone-5-carboxylate ion, a formate ion, an α-lipoate ion, a lactate ion, a tartrate ion, a hippurate ion, an N-methylhippurate ion, an N-benzoylalaninate ion, an N-acetylphenylalaninate ion, a 2,6-di-tert-butylphenol ion, a benzoate ion, an aspartate ion, a glycinate ion and an N-acetylglycinate ion; even more preferably an acetate ion, a 2-pyrrolidone-5-carboxylate ion, a lactate ion, a tartrate ion, a hippurate ion, an N-benzoylalaninate ion, a 2,6-di-tert-butylphenol ion, a benzoate ion, an N-acetylglycinate ion; still more preferably a 2-pyrrolidone-5-carboxylate ion, a lactate ion, a tartrate ion, a hippurate ion, an N-benzoylalaninate ion, an N-acetylglycinate ion; further more preferably a 2-pyrrolidone-5-carboxylate ion and a lactate ion.

Concretely, the ionic liquid suitable to this application is preferably 1-butyl-3-methylimidazolium hexafluorophosphate, 1-butyl-3-methylimidazolium lactate, N-methyl-N-propylpiperidinium bis(trifluoromethanesulfonyl)imidate, N-methyl-N-propylpyrrolidinium bis(trifluoromethanesulfonyl)imidate, N-hexylpyridinium bis(trifluoromethylsulfonyl)imidate, tetrabutylphosphonium 2-pyrrolidone-5-carboxylate, tetrabutylphosphonium acetate, tetrabutylphosphonium decanoate, tetrabutylphosphonium trifluoroacetate, tetrabutylphosphonium α-lipoate, tetrabutylphosphonium formate, tetrabutylphosphonium lactate, bis(tetrabutylphosphonium) tartrate, tetrabutylphosphonium hippurate, tetrabutylphosphonium N-methylhippurate, tetrabutylphosphonium benzoyl-DL-alaninate, tetrabutylphosphonium N-acetylphenylalaninate, tetrabutylphosphonium methanesulfonate, tetrabutylphosphonium 2,6-di-tert-butylphenol, tetrabutylphosphonium benzoate, monotetrabutylphosphonium L-aspartate, tetrabutylphosphonium glycinate, tetrabutylphosphonium N-acetylglycinate, 1-ethyl-3-methylimidazolium acetate, 1-ethyl-1-methylpiperidinium 2-pyrrolidone-5-carboxylate, 1-ethyl-3-methylimidazolium lactate, 1-ethyl-3-methylimidazolium hippurate, 1-ethyl-3-methylimidazolium 2-pyrrolidone-5-carboxylate, bis(1-ethyl-3-methylimidazolium) tartrate, 1-ethyl-3-methylimidazolium N-benzoyl-DL-alaninate, 1-ethyl-3-methylimidazolium N-acetylglycinate; more preferably tetrabutylphosphonium 2,6-di-tert-butylphenol, tetrabutylphosphonium benzoate, 1-ethyl-3-methylimidazolium acetate, 1-ethyl-1-methylpiperidinium 2-pyrrolidone-5-carboxylate, 1-ethyl-3-methylimidazolium lactate, 1-ethyl-3-methylimidazolium hippurate, 1-ethyl-3-methylimidazolium 2-pyrrolidone-5-carboxylate, bis(1-ethyl-3-methylimidazolium) tartrate, 1-ethyl-3-methylimidazolium N-benzoyl-DL-alaninate, 1-ethyl-3-methylimidazolium N-acetylglycinate; even more preferably 1-ethyl-1-methylpiperidinium 2-pyrrolidone-5-carboxylate, 1-ethyl-3-methylimidazolium lactate, 1-ethyl-3-methylimidazolium hippurate, 1-ethyl-3-methylimidazolium 2-pyrrolidone-5-carboxylate, bis(1-ethyl-3-methylimidazolium) tartrate, 1-ethyl-3-methylimidazolium N-benzoyl-DL-alaninate, 1-ethyl-3-methylimidazolium N-acetylglycinate; still more preferably 1-ethyl-1-methylpiperidinium 2-pyrrolidone-5-carboxylate, 1-ethyl-3-methylimidazolium lactate, 1-ethyl-3-methylimidazolium 2-pyrrolidone-5-carboxylate; further more preferably 1-ethyl-1-methylpiperidinium 2-pyrrolidone-5-carboxylate.

For producing the ionic liquid, herein employable are an anion exchange method that comprises reacting a precursor comprising a cation moiety such as an alkylimidazolium, alkylpyridinium, alkylammonium or alkylsulfonium ion and a halogen-containing anion moiety, with $NaBF_4$, $NaPF_6$, $CF_3SO_3Na$, $LiN(SO_2CF_3)_2$ or the like; an acid ester method comprising reacting an amine substance with an acid ester to introduce an alkyl group thereinto so that the organic acid residue could be a counter anion; and a neutralization method of neutralizing an amine with an organic acid to give a salt, to which, however, the invention should not be limited. In the neutralization method with an anion, a cation and a solvent, the anion and the cation are used both in the equivalent amount, and the solvent in the obtained reaction liquid is evaporated away, and the residue may be used directly as it is; or an organic solvent (e.g., methanol, toluene, ethyl acetate, acetone) may be further added thereto and the resulting liquid may be concentrated.

Although not specifically defined, the amount of the ionic liquid to be added may be any amount which is enough for resin curing; but preferably, it is from 0.01 to 30 parts by weight relative to 100 parts by weight of the ingredient (1). When the amount is less than 0.01 parts by weight, then the resin could not be cured sufficiently, but when it is more than 30 parts by weight, then the resin composition may lose storage stability. In the invention, the ionic liquid may serve as a curing agent for the ingredient (1) or as a curing accelerator when combined with any other curing agent. Accordingly, it is desirable that the amount of the ionic liquid is suitably controlled in accordance with the presence or absence of the other ingredients to be mentioned hereinunder. The lowermost limit of the amount of the ionic liquid to be added is more preferably 0.02 parts by weight relative to 100 parts by weight of the ingredient (1), from the viewpoint that it may exhibit good properties when used as a curing accelerator or as a curing agent, even more preferably 0.05 parts by weight, still more preferably 0.1 parts by weight, further more preferably 0.2 parts by weight, especially preferably 0.5 parts by weight. The uppermost limit of the amount of the ionic liquid to be added is more preferably 25 parts by weight relative to 100 parts by weight of the ingredient (1), from the viewpoint that it may exhibit good properties when used as a curing accelerator or as a curing agent, even more preferably 20 parts by weight, still more preferably 15 parts by weight, further more preferably 10 parts by weight, especially preferably 5 parts by weight.

Ingredient (3).

The resin composition comprising the ingredient (1) and the ingredient (2) of the invention may additionally comprise the ingredient (3), a polythiol compound having at least two thiol groups in the molecule, whereby its curing speed may be increased. Concretely, the compound includes trimethylolpropane tris(thioglycolate), pentaerythritol tetrakis(thioglycolate), ethylene glycol dithioglycolate, trimethylolpropane tris(β-thiopropionate), pentaerythritol tetrakis(β-thiopropionate), dipentaerythritol poly(β-thiopropionate). Also employable are thiol compounds having at least two thiol group in the molecule, which do not require use of a basic substance in their production, such as thiol compounds obtained through esterification of polyol and mercapto-organic acid.

Similarly, those that require a basic substance as the reaction catalyst in their production, for example, alkylpolythiol compounds such as 1,4-butane-dithiol, 1,6-hex ane-dithiol, 1,10-decane-dithiol; thiol-terminated polyethers; thiol-terminated polythioethers; thiol compounds prepared through reaction of epoxy compound and hydrogen sulfide; and thiol-terminated thiol compounds prepared through reaction of polythiol compound and epoxy compound may be processed for alkali removal, and the resulting thiol compounds with at least two thiol groups in the molecule having an alkali metal ion concentration of at most 50 ppm may be used herein.

For the alkali removal from the polythiol compound produced by the use of a basic substance as a reaction catalyst, for example, employable are a method comprising dissolving the polythiol compound to be processed in an organic solvent such as acetone or methanol, then adding an acid such as diluted hydrochloric acid or diluted sulfuric acid thereto for neutralization, and thereafter de-salting it by extraction, washing or the like; a method of using an ion exchange resin for adsorption; and a method of purification by distillation, to which, however, the invention should not be limited.

In the invention, the blend ratio of the ingredient (3) to the ingredient (1) is preferably from 0.2 to 1.2 in terms of the ratio of SH equivalence/epoxy equivalence. When it is less than 0.2, then the composition could not have sufficiently rapid curability; but on the other hand, when more than 1.2, then it may detract from the physical properties of the cured product such as the heat resistance thereof. From the viewpoint of enough adhesive strength, the ratio is more preferably from 0.5 to 1.0.

Ingredient (4).

The resin composition comprising the ingredient (1) and the ingredient (2), or the resin composition comprising the ingredient (1), the ingredient (2) and the ingredient (3) of the invention may further comprise the ingredient (4), a compound having Lewis acidity, whereby its storage stability may be enhanced. Concretely, the compound includes titanate compounds, borate compounds, aluminate compounds and zirconate compounds.

Typical examples of the borates are trimethyl borate, triethyl borate, tri-n-propyl borate, triisopropyl borate, tri-n-butyl borate, tripentyl borate, triallyl borate, trihexyl borate, tricyclohexyl borate, trioctyl borate, trinonyl borate, tridecyl borate, tridodecyl borate, trihexadecyl borate, trioctadecyl borate, tris(2-ethylhexyloxy)borane, bis(1,4,7,10-tetraoxaundecyl)(1,4,7,10,13-pentaoxatetradecyl)(1,4,7-trioxaundecyl)borane, tribenzyl borate, triphenyl borate, tri-O-tolyl borate, tri-m-tolyl borate, triethanolamine borate.

The titanates include tetraethyl titanate, tetrapropyl titanate, tetraisopropyl titanate, tetrabutyl titanate, tetraoctyl titanate.

The aluminate compounds include triethyl aluminate, tripropyl aluminate, triisopropyl aluminate, tributyl aluminate, trioctyl aluminate.

The zirconate compounds include tetraethyl zirconate, tetrapropyl zirconate, tetraisopropyl zirconate, tetrabutyl zirconate.

Of those, preferred are the borates from the viewpoint of good general-purpose applicability and safety and excellent storage stability thereof; more preferred are triethyl borate, tri-n-propyl borate, triisopropyl borate, tri-n-butyl borate; even more preferred is triethyl borate. Although not specifically defined, the amount of the borate to be added may be any amount capable of increasing the storage stability of resin; but preferably it is from 0.001 to 3.0 parts by weight relative to 100 parts by weight of epoxy resin. When the amount is less than 0.001 parts by weight, then the expected storage stability could not be obtained; but when more than 3.0 parts by weight, then the curing time may be long. From the viewpoint of the balance of good curability and good storage stability, the amount is more preferably from 0.5 to 2.0 parts by weight.

Ingredient (5).

The resin composition comprising the ingredient (1) and the ingredient (2) of the invention may further comprise an acid anhydride (5) as a curing agent. The acid anhydride includes tetrahydrophthalic anhydride, methyltetrahydrophthalic anhydride, hexahydrophthalic anhydride, methylhexahydrophthalic anhydride, methylnadic anhydride, dodecenylsuccinic anhydride; and one or more of these may be used either singly or as combined.

Comprising a combination of the above-mentioned ingredients (1) to (5), the resin composition of the invention may have desired curing capability, and the cured product may have good strength and stability. For example, for increasing the curing speed, one or more desired ingredients may be selected from the ingredients (2), (3) and (5), and their amount added may be controlled. On the other hand, for obtaining long-term storage stability, for example, the amount of the ingredient (4) to be added is preferably controlled.

The method for curing the resin composition of the invention is not specifically defined. In accordance with the field in which the composition is used, the method for curing it may be suitably selected and used. For example, usable are a hot air circulating oven, an IR heater, a heat gun, a high-frequency induction heater, and a heat tool for pressure heating. The curing condition may be grouped into low-temperature long-time curing and high-temperature short-time curing depending on the apparatus used and the object thereof; and in consideration of overheating deterioration prevention and energy saving of the members to be used along with the resin composition of the invention, preferred temperature range and time may be selected.

In the invention, the "practicable curing temperature" may be considered as follows: From the viewpoint that the members to be used along with the composition of the invention are prevented from being deteriorated by overheating and that the energy used for curing is saved, an ordinary uppermost limit of the curing temperature is preferably 250° C., more preferably 200° C., even more preferably 180° C., still more preferably 160° C., further preferably 140° C., still further preferably 120° C. On the other hand, an ordinary lowermost limit of the curing temperature is, from the viewpoint that the composition may be cured while keeping its practicable storage stability, preferably 50° C., more preferably 55° C.

In particular, in the case where the parts to be used along with the resin composition of the invention comprise a plastic material, the uppermost limit of the curing temperature is preferably 150° C., more preferably 120° C., even more preferably 100° C., still more preferably 80° C., further more preferably 60° C. On the other hand, from the viewpoint that the composition may be cured while keeping its practicable storage stability, the lowermost limit of the curing temperature is preferably 50° C., more preferably 55° C.

In particular, in case where the parts to be used along with the resin composition of the invention comprise a magnetic material, the uppermost limit of the curing temperature is, from the viewpoint of reducing the deterioration of the magnetic material by heat, preferably 180° C., more preferably 150° C., even more preferably 120° C., still more preferably 100° C. From the viewpoint that the composition may be cured while keeping its practicable storage stability, the lowermost limit of the curing temperature is preferably 50° C., more preferably 55° C.

In the invention, "practicable gelling time (gel time)" means the time for gelling at the production field; and in general, it is preferably shorter for improving the producibility. Though depending on the curing temperature, the uppermost limit of the practicable gelling time is preferably 120 minutes, more preferably 90 minutes, even more preferably 60 minutes, still more preferably 30 minutes, further more preferably 15 minutes. Though the time is preferably shorter, the lowermost limit of the practicable gelling time is, from the viewpoint of time controllability, preferably 0.001 seconds, more preferably 0.1 seconds. In particular, in case where the composition is heated by leading it to pass through a heater with a belt conveyor or the like, and when the composition is required to be cured relatively instantly, the uppermost limit of the practicable gelling time is preferably 15 minutes, more preferably 5 minutes, even more preferably 3 minutes, still more preferably 1 minute, further more preferably 30 seconds. Though the time is preferably shorter, the lowermost limit of the practicable gelling time is, from the viewpoint of time controllability, preferably 0.001 seconds, more preferably 0.1 seconds.

In the invention, "practicable storage stability" means the stability during the period of from production to practical use, and further during the period of from commercial distribution to practical use by buyers. In case where the composition is used after commercial distribution or after long-term storage, its storage stability may be enhanced by storing it at a low temperature, for example, in refrigerators, freezers, etc. In general, from the viewpoint that the composition may be well commercially distributed at an environmental temperature of from 20° C. to 40° C., the lowermost limit of the storage stability is preferably 3 hours, more preferably 6 hours, even more preferably 12 hours, still more preferably 1 day, further more preferably 3 days, especially preferably 7 days. In general, from the viewpoint that the composition may be well commercially distributed at an environmental temperature of from 20° C. to 40° C., the uppermost limit of the storage stability is preferably 2 weeks, more preferably 3 weeks, even more preferably 1 month, still more preferably 2 months, further more preferably 3 months, especially preferably 6 months.

In the invention, "practicable curing time" differs from "time from the start of curing to the finish of curing" generally referred to in the art; and it means "time between the reaction start time (heat generation start time) and the reaction end time (heat generation end time) in the heat generation curve in differential scanning calorimetry (DSC)". From the viewpoint of uniform curability, it is desirable that the curve gives a sharp peak and the curing time is shorter. Concretely, the lowermost limit of the curing time is preferably shorter, and is preferably 0.001 minutes. Not specifically defined, the uppermost limit of the curing time may be any one within which the composition may cure; but from the viewpoint of uniform curability with no unevenness, it is preferably 60 minutes, more preferably 30 minutes, even more preferably 20 minutes, still more preferably 10 minutes, further more preferably 5 minutes.

Various additives may be added to the resin composition of the invention, not detracting from the advantages thereof, and they include fillers, diluents, solvents, pigments, flexibility-imparting agents, coupling agents, antioxidants, defoaming agents, etc.

The resin composition of the invention has excellent curability and, especially when an ambient temperature ionic liquid is used therein, the composition is completely liquid and is therefore favorable mainly for applications of fine chemical products such as adhesives, sealing agents, casting materials, etc. In particular, the composition is most favorable for applications of coil impregnation sealing, relay sealing, and so-called impregnation adhesion to be attained by casting the composition into a space via which the parts to be stuck are contacted with each other; for these, however, conventional impregnation-type adhesives are unfavorable as forming uncured faults. As paints and coating agents, the composition is utilizable for insulating paints for printed wire boards and for moisture-resistant coatings for various electronic parts.

In a another aspect thereof, the present invention provides novel ionic liquids that are useful as a curing agent and/or a curing accelerator in the above-mentioned resin composition. The ionic liquid comprises (a) a cation selected from a tetraalkylphosphonium ion, preferably a tetrabutylphosphonium ion, and (b) an anion selected from an α-lipoate ion, a lactate ion, a tartrate ion, a hippurate ion, an N-methylhippurate ion, an N-benzoylalaninate ion, an N-acetylphenylalaninate ion, a 2-pyrrolidone-5-carboxylate ion and an N-acetylglycinate ion. The ionic liquid may be used as the curing agent for the above-mentioned ingredient (1) by itself, and therefore, the constitution of the resin composition may be simplified and may be readily produced. In general, when a thiol-based curing agent is added to an epoxy resin composition, then the curing speed may be increased; but on the other hand, there is a problem in that the moisture resistance and the heat resistance of the cured products are lowered. However, the ionic liquid in the invention may exhibit its excellent curing effect by itself, and therefore can solve the problem. In addition, it may exhibit various functions of ionic liquid, for example, as an antistatic agent, a solvent, a flame retardant, etc.

Other features of the invention will become apparent in the course of the following descriptions of exemplary embodiments which are given for illustration of the invention and are not intended to be limiting thereof.

EXAMPLES

Evaluation Methods
Appearance Test for Adhesive.

A resin composition was put into a 50-mL sample bottle of glass, and visually checked as to whether it is transparent (not colored, and it looks clear through the sample bottle), or semitransparent (somewhat colored, but it looks clear through the sample bottle), or opaque (colored, and it could not look clear through the sample bottle).

Test for Measurement of Gelling Time.

Each composition was tested with a hot plate-type gelling tester (GT-D, by Nisshin Science) according to JIS C6521, in which the time in which the sample became no cobwebbier at 150° C. was measured. Concretely, about 0.5 g of a resin is put on the hot plate-type gelling tester, and at 150° C., a stopwatch is started. A spatula having a tip width of 5 mm is repeatedly moved to give a contact circular motion to the resin, and the time for the resin gellation is measured. The contact circular motion is as follows: The resin is held to be within a range having a diameter of 25 mm. The spatula is not pulled up while the viscosity of the resin is low, and is moved for 1 rotation for 1 second. After the viscosity has increased, the resin is sometimes lifted up from the hot plate vertically thereto by about 30 mm, and the vertical motion is repeated until the cobwebby gel is cut. One sample is tested three times, and the data are averaged to be the gelling time.

Storage Stability Test.

A prepared resin composition was put into a 50-mL polypropylene bottle (plastic bottle by Yamayu), and the time (day) in which it was gelled at 30° C. was measured.

Impregnation Adhesiveness Test.

The surface of a test piece of a mild steel plate (JISG3141, SPCCD) was polished with an endless belt (JIS #120). The roughness of the polished surface was measured with a three-dimensional interference microscope (Veeco Metorology's "WykoNT 3300"), and the polished depth was from 3 to 8 μm on one surface. The polished surfaces were stuck, as overlapped by 12 mm, and compacted under pressure with two clips. At the edge of one of the thus-stuck test pieces was coated with the composition prepared in each Example to a thickness of about 3 mm, then these were stood diagonally in an oven, and heated and cured at 170° C. for 60 minutes in the condition in which the adhesive could easily penetrate into the affixed part, and thus adhered. After cured, the steel plates were peeled and the adhered surface was checked. The samples with no tack on the adhered surface, in which the composition was uniformly cured, are good (O); and those with some uncured tacks remaining thereon are bad (x).

Thin Film Curability Test.

The composition prepared in each Example was applied to the steel plate polished in the same manner as in the above adhesiveness test through impregnation to mild steel plates, using a bar coater of which the thickness was 20 µm. The coating film was heated and cured at 170° C. for 60 minutes. The thickness of the coating film after cured was from 10 to 20 µm. The samples with a uniformly cured coating film are good (O); and those with a ununiform and rough coating film are bad (x).

Measurement of Curing Time.

In general, curing time means the time from the start of curing to the end of curing; but in the following Examples, curing time is the time difference between the reaction start time (heat generation start time) and the reaction end time (heat generation end time) in the heat generation curve in differential scanning calorimetry (DSC). The method of measurement was as follows: Using Seiko Instruments' differential scanning calorimeter DSC6200, about 2 mg of a sample was heated from 25° C. up to 250° C. at a heating rate of 5° C./min, and the heat generation curve was analyzed (see, FIG. 1).

The abbreviations of the materials used in the following Examples are mentioned below.

(1) Epoxy Resin:
"EP-828" (trade name by Japan Epoxy Resin); bisphenol A-type epoxy resin, having an epoxy equivalent of from 184 to 194.

(2) Episulfide Resin:
"YL7007" (trade name by Japan Epoxy Resin), having an episulfide equivalent of 220.

(3) Polythiol Compound:
"TMTP" (trade name by Yodo Chemical); trimethylolpropane tris(0-thiopropionate).

(4) Silane Coupling Agent:
"KBM403" (by Shin-etu Chemical Industry).

(5) Hydrophobic Silica:
"Aerosil RY200" (by Nippon Aerosil).

Production Example 1

5.0 g of (S)-(−)-2-pyrrolidone-5-carboxylic acid (by Wako Pure Chemical Industries) was suspended in 30 ml of methanol, and 26.8 g of aqueous 40% tetrabutylphosphonium hydroxide (by Aldrich) was dropwise added thereto at 0° C., taking 3 minutes. After being stirred for 10 minutes, this was concentrated under reduced pressure at 40° C., using an evaporator. 50 ml of methanol was added to the residue, and the mixture was concentrated under reduced pressure in the same manner. 100 ml of toluene was added to the obtained residue, and the resulting mixture was concentrated under reduced pressure; and this operation was repeated twice. Next, this was concentrated in ultra-high vacuum at from room temperature to 50° C. for 15 hours. 15.3 g of tetrabutylphosphonium (S)-(−)-2-pyrrolidone-5-carboxylate (purity, 98.0%) was obtained as an oily compound. (This is an ionic liquid A.) In NMR analysis, neither toluene nor methanol was detected.

NMR Spectrum:
1HNMR (CDCl$_3$) δ: 0.77-0.93 (m, 12H), 1.30-1.49 (m, 16H), 2.02-2.12 (m, 1H), 2.12-2.23 (m, 10H), 2.23-2.33 (m, 1H), 3.92-3.97 (m, 1H), 6.25 (br s, 1H)

The purity was computed as follows: "Purity (%)=theoretical weight (g)/found yield weight (g)×100"

Similarly, various phosphonium salts (Production Examples 2 to 16) were prepared. Various imidazolium salts (Production Examples 17 and 19 to 25) and piperidinium salt (Production Example 18) were prepared similarly to the above, for which, however, used was 1-ethyl-3-methylimidazolium hydrogencarbonate (50% solution, by Aldrich) or 1-ethyl-1-methylpiperidinium methylcarbonate (50% solution, by Aldrich). The results are shown in Table 1.

TABLE 1

| Production Example | Compound | Purity (%) | Morphology (50° C.) | Remarks |
|---|---|---|---|---|
| 2 | tetrabutylphosphonium trifluoroacetate | 96.62 | oil | |
| 3 | tetrabutylphosphonium α-lipoate | 94.50 | oil | |
| 4 | tetrabutylphosphonium formate | 96.02 | oil | |
| 5 | tetrabutylphosphonium (L)-lactate | 97.99 | oil | |
| 6 | bis(tetrabutylphosphonium) L-tartrate | 94.98 | oil | |
| 7 | tetrabutylphosphonium hippurate | 95.49 | solid | m.p. 75° C. |
| 8 | tetrabutylphosphonium N-methylhippurate | 96.20 | oil | |
| 9 | tetrabutylphosphonium benzoyl-DL-alaninate | 96.54 | oil | |
| 10 | tetrabutylphosphonium N-acetyl-L-phenylalaninate | 96.26 | oil | |
| 11 | tetrabutylphosphonium methanesulfonate | 95.71 | solid | m.p. 62° C. |
| 12 | tetrabutylphosphonium 2,6-di-tert-butylphenol | 97.11 | solid | m.p. 125-128° C. |
| 13 | tetrabutylphosphonium benzoate | 95.67 | oil | |
| 14 | monotetrabutylphosphonium L-aspartate | 96.67 | oil | |
| 15 | tetrabutylphosphonium glycinate | 95.56 | oil | |
| 16 | tetrabutylphosphonium N-acetylglycinate | 97.20 | oil | |
| 17 | 1-ethyl-3-methylimidazolium acetate | 97.03 | oil | |

TABLE 1-continued

| Production Example | Compound | Purity (%) | Morphology (50° C.) | Remarks |
|---|---|---|---|---|
| 18 | 1-ethyl-1-methylpiperidinium (S)-(−)-2-pyrrolidone-5-carboxylate | 90.37 | oil | |
| 19 | 1-ethyl-3-methylimidazolium (L)-lactate | 97.33 | oil | |
| 20 | 1-ethyl-3-methylimidazolium formate | 89.06 | oil | |
| 21 | 1-ethyl-3-methylimidazolium hippurate | 91.47 | oil | |
| 22 | 1-ethyl-3-methylimidazolium (S)-(−)-2-pyrrolidone-5-carboxylate | 93.18 | oil | |
| 23 | bis(1-ethyl-3-methylimidazolium) (L)-tartrate | 95.60 | oil | |
| 24 | 1-ethyl-3-methylimidazolium N-benzoyl-DL-alaninate | 94.33 | oil | |
| 25 | 1-ethyl-3-methylimidazolium N-acetylglycinate | 94.96 | oil | |

Example 1

100 parts by weight of "EP828", 59 parts by weight of "TMTP", 1.4 parts by weight of triethyl borate and 0.3 parts by weight of the ionic liquid shown in Production Example 1 were mixed with a mixture at room temperature for 30 minutes.

Examples 2 to 14

Using commercial ionic liquids B to G and in accordance with the formulation shown in Table 2 and Table 3 below, resin compositions of Examples 2 to 14 were obtained in the same manner as in Example 1. The amount of the material shown in the Tables is in terms of part by weight. The obtained resin compositions were tested and evaluated for the appearance of adhesive, the storage stability, the gelling time, the impregnation adhesiveness, and the thin film curability. The results are shown in Table 2 and Table 3.

TABLE 2

| Material | Example 1 | Example 2 | Example 3 | Example 4 | Example 5 | Example 6 | Example 7 |
|---|---|---|---|---|---|---|---|
| Bisphenol A-type Epoxy Resin "EP828" | 100 | 100 | 100 | 100 | 100 | 100 | 100 |
| Ionic Liquid A | 0.3 | | | | | | |
| Ionic Liquid B | | 0.3 | | | | | |
| Ionic Liquid C | | | 0.4 | | | | |
| Ionic Liquid D | | | | 0.22 | | | |
| Ionic Liquid E | | | | | 0.59 | | 0.59 |
| Ionic Liquid F | | | | | | 0.38 | |
| Ionic Liquid G | | | | | | | |
| Polythiol "TMTP" | 59 | 59 | 59 | 59 | 59 | 59 | 59 |
| Triethyl Borate | 1.4 | 1.4 | 1.4 | 1.4 | 2.1 | 2.1 | |
| Silane Coupling Agent "KBM403" | 1 | 1 | 1 | 1 | 1 | 1 | 1 |
| Hydrophobic Silica "RY200" | 1 | 1 | 1 | 1 | 1 | 1 | 1 |
| Appearance of Adhesive | transparent | transparent | transparent | transparent | transparent | transparent | transparent |
| Gelling Time | 34 sec | 20 sec | 31 sec | 1 min 35 sec | 8 min 30 sec | 6 min | 5 min 45 sec |
| Storage Stability (day) | 28 | 17 | 26 | 57 | >60 | >60 | 48 |
| Impregnation Adhesiveness | ◯ | ◯ | ◯ | ◯ | ◯ | ◯ | ◯ |
| Thin Film Curability | ◯ | ◯ | ◯ | ◯ | ◯ | ◯ | ◯ |
| Storage Stability/Gelling Time (day/sec) | 0.8235 | 0.8500 | 0.8387 | 0.60000 | 0.1176 | 0.1667 | 0.1391 |

TABLE 3

| Material | Example 8 | Example 9 | Example 10 | Example 11 | Example 12 | Example 13 | Example 14 |
|---|---|---|---|---|---|---|---|
| Bisphenol A-type Epoxy Resin "EP828" | 100 | 100 | 100 | 100 | 100 | 100 | 100 |
| Ionic Liquid A | | | | | | | |
| Ionic Liquid B | | | | | | | |
| Ionic Liquid C | | | | | | | |
| Ionic Liquid D | | | | | | | |
| Ionic Liquid E | | | | 3 | 3 | | |
| Ionic Liquid F | | | | | | 3 | 3 |
| Ionic Liquid G | 0.27 | 0.27 | 0.27 | | | | |
| Polythiol "TMTP" | 59 | 59 | 59 | 59 | 59 | 59 | 59 |
| Triethyl Borate | 2.1 | 1 | | 2.1 | | 2.1 | 2.1 |
| Silane Coupling Agent "KBM403" | 1 | 1 | 1 | 1 | 1 | 1 | |
| Hydrophobic Silica "RY200" | 1 | 1 | 1 | 1 | 1 | 1 | |
| Appearance of Adhesive | transparent | transparent | transparent | transparent | transparent | transparent | transparent |
| Gelling Time | 6 min 40 sec | 6 min 30 sec | 18 sec | 6 min 40 sec | 6 min 40 sec | 5 min 30 sec | 5 min 25 sec |
| Storage Stability (day) | >60 | 34 | <3 | 41 | 36 | 43 | 43 |
| Impregnation Adhesiveness | ○ | ○ | ○ | ○ | ○ | ○ | ○ |
| Thin Film Curability | ○ | ○ | ○ | ○ | ○ | ○ | ○ |
| Storage Stability/Gelling Time (day/sec) | 0.1500 | 0.0872 | 0.1667 | 0.1025 | 0.0900 | 0.1303 | 0.1323 |

Ionic Liquid A: tetrabutylphosphonium (S)-(−)-2-pyrrolidone-5-carboxylate (Production Example 1).
Ionic Liquid B: tetrabutylphosphonium acetate (by Hokko Chemical).
Ionic Liquid C: tetrabutylphosphonium decanoate (by Hokko Chemical).
Ionic Liquid D: 1-butyl-3-methylimidazolium (L)-lactate (by Kanto Chemical).
Ionic Liquid E: N-methyl-N-propylpiperidinium bis(trifluoromethanesulfonyl)imidate (by Kanto Chemical).
Ionic Liquid F: N-methyl-N-propylpyrrolidinium bis(trifluoromethanesulfonyl)imidate (by Kanto Chemical).
Ionic Liquid G: 1-butenyl-3-methylimidazolium hexafluorophosphate (by Kanto Chemical).

From the results in Table 2, it was confirmed that addition of a small amount of an ionic liquid secures rapid curability and storage stability. The curing speed differs depending on the type of the ionic liquid, but the curing speed may be controlled by controlling the amount of the ionic liquid to be added to the resin composition. To the samples containing any of the ionic liquids E to G and having a relatively low curing speed, the amount of triethyl borate to be added was varied. It was confirmed that the reactivity-retarding effect by the addition of triethyl borate was noticeable with the ionic liquid G, but was low with the ionic liquid E. Addition of a silane coupling agent improves the adhesiveness to metal; and addition of hydrophobic silica is effective for suppressing the flowability in the thin film curing test; however, it was confirmed that they have no influence on the curing speed and the storage stability.

Examples 15 to 20

Next, resin compositions of Examples 15 to 20 were prepared by mixing an epoxy resin and an episulfide resin as the ingredient (1) in the invention, according to the formulation shown in Table 4; and these were tested and evaluated in the same manner as above. The results are shown below.

TABLE 4

| Material | Example 15 | Example 16 | Example 17 | Example 18 | Example 19 | Example 20 |
|---|---|---|---|---|---|---|
| Bisphenol A-type Epoxy Resin "EP828" | 100 | 80 | 60 | 40 | 20 | |
| Episulfide "YL7007" | | 20 | 40 | 60 | 80 | 100 |
| Ionic Liquid C | 0.4 | 0.4 | 0.4 | 0.4 | 0.4 | 0.4 |
| Polythiol "TMTP" | 52 | 50 | 49 | 47 | 46 | 45 |
| Triethyl Borate | 1.4 | 1.4 | 1.4 | 1.4 | 1.4 | 1.4 |
| Appearance of Adhesive | transparent | transparent | transparent | transparent | transparent | transparent |
| Gelling Time | 26 sec | 20 sec | 19 sec | 19 sec | 15 sec | 15 sec |
| Storage Stability (day) | 16 | 21 | 18 | 21 | 20 | 22 |
| Impregnation Adhesiveness | ○ | ○ | ○ | ○ | ○ | ○ |
| Thin Film Curability | ○ | ○ | ○ | ○ | ○ | ○ |
| Storage Stability/Gelling Time (day/sec) | 0.6154 | 1.0500 | 0.9474 | 1.1053 | 1.3333 | 1.4667 |

(Notes)
Ionic Liquid C: tetrabutylphosphonium decanoate (by Hokko Chemical).

From the results in Table 4, it was confirmed that addition of episulfide resin to epoxy resin enhanced the curability and improved the storage stability in some degree without any problem in use of the resin composition.

Examples 21 to 36

Resin compositions of Examples 21 to 36 were prepared according to the formulation shown in Tables 5 and 6, and tested and evaluated in the same manner as above. These are for confirming whether or not the ionic liquid alone could function as a curing agent in the absence of the ingredient (3), polythiol compound. The results are shown in Table 5 and Table 6.

TABLE 5

| Material | Example 21 | Example 22 | Example 23 | Example 24 | Example 25 | Example 26 | Example 27 | Example 28 | Example 29 | Example 30 |
|---|---|---|---|---|---|---|---|---|---|---|
| Bisphenol A-type Epoxy Resin "EP828" | 100 | 100 | 100 | 100 | 100 | 100 | 100 | 100 | 100 | 100 |
| Episulfide "YL7007" | | | | | | | | | | |
| Ionic Liquid A | | | 5 | | | | | | 5 | |
| Ionic Liquid B | | | | 4 | | | 4 | | | |
| Ionic Liquid C | | | | | 6 | | | 6 | | |
| Ionic Liquid D | 1 | 3 | | | | 3 | | | | |
| Ionic Liquid E | | | | | | | | | | |
| Ionic Liquid F | | | | | | | | | | |
| Ionic Liquid G | | | | | | | | | | 4 |
| Triethyl Borate | | | | | | 1 | 1 | 1 | 1 | |
| Appearance of Adhesive | transparent | transparent | transparent | transparent | transparent | transparent | transparent | transparent | transparent | transparent |
| Gelling Time | >60 min | 1 min 25 sec | 18 sec | 7 sec | 7 sec | 21 min 30 sec | 20 sec | 14 sec | 3 min 20 sec | >60 min |
| Storage Stability (day) | >60 | 24 | 27 | 1 | <1 | 40 | 4 | 2 | 37 | — |
| Impregnation Adhesiveness | — | ○ | ○ | ○ | ○ | ○ | ○ | ○ | ○ | — |
| Thin Film Curability | — | ○ | ○ | ○ | ○ | ○ | ○ | ○ | ○ | — |
| Storage Stability/Gelling Time (day/sec) | 0.0167 | 0.2824 | 1.5000 | 0.1429 | 0.1429 | 0.0310 | 0.2000 | 0.1429 | 0.1850 | — |

TABLE 6

| Material | Example 31 | Example 32 | Example 33 | Example 34 | Example 35 | Example 36 |
|---|---|---|---|---|---|---|
| Bisphenol A-type Epoxy Resin "EP828" | 100 | 100 | 50 | | | |
| Episulfide "YL7007" | | | 50 | 100 | 100 | 100 |
| Ionic Liquid A | | | 5 | 5 | 5 | |
| Ionic Liquid B | | | | | | 4 |
| Ionic Liquid C | | | | | | |
| Ionic Liquid D | | | | | | |
| Ionic Liquid E | 6 | | | | | |
| Ionic Liquid F | | 5 | | | | |
| Ionic Liquid G | | | | | | |
| Triethyl Borate | | | 1 | 1 | | 1 |
| Appearance of Adhesive | transparent | transparent | transparent | transparent | transparent | transparent |
| Gelling Time | >60 min | >60 min | 27 sec | 5 sec | — | — |
| Storage Stability (day) | — | — | 17 | <2 hrs | <1 hr | <5 min |
| Storage Stability/Gelling Time (day/sec) | — | — | 0.6296 | 0.0167 | — | — |

Ionic liquids A to G are the same as in Table 3.

The results in Table 5 show that the ionic liquids A, B, C and D have the function of curing epoxy resin when used alone. Addition of triethyl borate retards the reactivity and improved the storage stability; but it was confirmed that even though it was not added to the liquids A and D, the curability was still good and the storage stability was on the level with no practical problem. The results in Table 6 show that the application of ionic liquid to episulfide resin promotes the curability but lower the storage stability; and it is presumed that reducing the amount of the ionic liquid may improve the storage stability. As the base resin in single use of ionic liquid as a curing agent, episulfide resin may be practicable.

Examples 37 to 52

The ionic liquids H to W newly synthesized in the above Production Example were used and investigated for the curing epoxy resin. The results are shown below.

TABLE 7

| Material | Example 37 | Example 38 | Example 39 | Example 40 | Example 41 | Example 42 | Example 43 | Example 44 |
|---|---|---|---|---|---|---|---|---|
| Bisphenol A-type Epoxy Resin "EP828" | 100 | 100 | 100 | 100 | 100 | 100 | 100 | 100 |
| Ionic Liquid H | 4.8 | | | | | | | |
| Ionic Liquid I | | 6.1 | | | | | | |
| Ionic Liquid J | | | 4 | | | | | |
| Ionic Liquid K | | | | 4.6 | | | | |
| Ionic Liquid L | | | | | 4.4 | | | |
| Ionic Liquid M | | | | | | 5.8 | | |
| Ionic Liquid N | | | | | | | 5.9 | |
| Ionic Liquid O | | | | | | | | 5.9 |
| Appearance of Adhesive | transparent | transparent | transparent | transparent | transparent | transparent | transparent | transparent |
| Gelling Time | 13 min 50 sec | 16 sec | 16 sec | 55 sec | 1 min 7 sec | 1 min 25 sec | 23 sec | 44 sec |
| Curing Time (min) | 11.7 | 15.6 | 10.6 | 6.4 | 12.5 | 13.4 | 14.4 | 13.9 |
| Storage Stability (day) | >60 | 2 | 28 | 28 | 6 | 28 | 3 | 22 |
| Storage Stability/Gelling Time (day/sec) | 0.0723 | 0.1250 | 1.7500 | 0.5091 | 0.0896 | 0.3294 | 0.1304 | 0.5000 |

TABLE 8

| Material | Example 45 | Example 46 | Example 47 | Example 48 | Example 49 | Example 50 | Example 51 | Example 52 |
|---|---|---|---|---|---|---|---|---|
| Bisphenol A-type Epoxy Resin "EP828" | 100 | 100 | 100 | 100 | 100 | 100 | 100 | 100 |
| Ionic Liquid P | 6.1 | | | | | | | |
| Ionic Liquid Q | | 4.7 | | | | | | |
| Ionic Liquid R | | | 6.1 | | | | | |
| Ionic Liquid S | | | | 5 | | | | |
| Ionic Liquid T | | | | | 5.2 | | | |
| Ionic Liquid U | | | | | | 4.4 | | |
| Ionic Liquid V | | | | | | | 4.9 | |
| Ionic Liquid W | | | | | | | | 3 |
| Appearance of Adhesive | transparent | transparent | transparent | transparent | transparent | transparent | transparent | transparent |
| Gelling Time | 30 sec | >60 min | 22 sec | 11 sec | 1 min 25 sec | 1 min 40 sec | 1 min | >90 min |
| Curing Time (min) | 15.6 | >40 | 10.7 | 15.6 | 6.2 | 7.8 | 9.8 | >40 |
| Storage Stability (day) | 4 | >60 | 3 | 1 | 10 | 14 | 42 | >60 |
| Storage Stability/Gelling Time (day/sec) | 0.1333 | 0.0167 | 0.1364 | 0.0909 | 0.1176 | 0.1400 | 0.7000 | 0.0111 |

Notes to Table 8.
Ionic Liquid H: tetrabutylphosphonium trifluoroacetate (Production Example 2).
Ionic Liquid I: tetrabutylphosphonium α-lipoate (Production Example 3).
Ionic Liquid J: tetrabutylphosphonium formate (Production Example 4).
Ionic Liquid K: tetrabutylphosphonium (L)-lactate (Production Example 5).
Ionic Liquid L: tetrabutylphosphonium L-tartrate (Production Example 6).
Ionic Liquid M: tetrabutylphosphonium hippurate (Production Example 7).
Ionic Liquid N: tetrabutylphosphonium N-methylhippurate (Production Example 8).
Ionic Liquid O: tetrabutylphosphonium benzoyl-DL-alaninate (Production Example 9).
Ionic Liquid P: tetrabutylphosphonium N-acetyl-L-phenylalaninate (Production Example 10).
Ionic Liquid Q: tetrabutylphosphonium methanesulfonate (Production Example 11).
Ionic Liquid R: tetrabutylphosphonium 2,6-di-tert-butylphenol (Production Example 12).
Ionic Liquid S: tetrabutylphosphonium benzoate (Production Example 13).
Ionic Liquid T: tetrabutylphosphonium L-aspartate (Production Example 14).
Ionic Liquid U: tetrabutylphosphonium glycinate (Production Example 15).
Ionic Liquid V: tetrabutylphosphonium N-acetylglycinate (Production Example 16).
Ionic Liquid W: 1-butyl-3-methylimidazolium tetrafluoroborate (by Kanto Chemical).

With the ionic liquids Q and W used in the amount as indicated, the gelling time (gel time) at 150° C. was longer than 1 hour, and it was hard to say that they might be always practicable. Depending on the type of the ionic liquid, the gelling time, the curing speed and the storage stability fluctuate. As practicable curing agents with which the gelling time was within 10 minutes and the storage stability was not shorter than 10 days, preferred were the ionic liquids J, K, M, O, T, U, and V. Further, it was confirmed that the ionic liquids taking a curing time of not longer than 10 minutes, or that was, the ionic liquid A (8.2 min), the ionic liquid K (6.4 min), the ionic liquid T (6.2 min), and the ionic liquid U (7.8 min) were especially favorable as they were excellent in the degree of reaction completion. For reference, the data of differential scanning calorimetry (DSC) of Examples 47 to 51 (with ionic liquids R, S, T, U and V) are shown in FIG. 1.

Examples 53 to 67

Using the ionic liquids H to W, triethyl borate-comprising epoxy resins were tested for the curing speed and the storage stability.

TABLE 9

| Material | Example 53 | Example 54 | Example 55 | Example 56 | Example 57 | Example 58 | Example 59 | Example 60 |
|---|---|---|---|---|---|---|---|---|
| Bisphenol A-type Epoxy Resin "EP828" | 100 | 100 | 100 | 100 | 100 | 100 | 100 | 100 |
| Ionic Liquid H | 4.8 | | | | | | | |
| Ionic Liquid I | | 6.1 | | | | | | |
| Ionic Liquid J | | | 4 | | | | | |
| Ionic Liquid K | | | | 4.6 | | | | |
| Ionic Liquid L | | | | | 4.4 | | | |
| Ionic Liquid M | | | | | | 5.8 | | |
| Ionic Liquid N | | | | | | | 5.9 | |
| Ionic Liquid O | | | | | | | | 5.9 |
| Triethyl Borate | 1 | 1 | 1 | 1 | 1 | 1 | 1 | 1 |
| Appearance of Adhesive | transparent | transparent | transparent | transparent | transparent | transparent | transparent | transparent |
| Gelling Time | >60 min | 11 min 50 sec | 11 min 50 sec | 13 min 40 sec | 33 min 20 sec | 12 min 30 sec | 2 min | 5 min 20 sec |
| Storage Stability (day) | >60 | 4 | 42 | 51 | >60 | 51 | 27 | 42 |
| Storage Stability/Gelling Time (day/sec) | 0.0167 | 0.0056 | 0.0592 | 0.0622 | 0.0300 | 0.0680 | 0.2250 | 0.1313 |

TABLE 10

| Material | Example 61 | Example 62 | Example 63 | Example 64 | Example 65 | Example 66 | Example 67 |
|---|---|---|---|---|---|---|---|
| Bisphenol A-type Epoxy Resin "EP828" | 100 | 100 | 100 | 100 | 100 | 100 | 100 |
| Ionic Liquid P | 6.1 | | | | | | |
| Ionic Liquid R | | 6.1 | | | | | |
| Ionic Liquid S | | | 5 | | | | |
| Ionic Liquid T | | | | 5.2 | | | |
| Ionic Liquid U | | | | | 4.4 | | |
| Ionic Liquid V | | | | | | 4.9 | |
| Ionic Liquid W | | | | | | | 3 |
| Triethyl Borate | 1 | 1 | 1 | 1 | 1 | 1 | 1 |
| Appearance of Adhesive | transparent | transparent | Transparent | transparent | transparent | transparent | transparent |
| Gelling Time | 7 min 40 sec | 34 min 20 sec | 24 min 30 sec | 9 min 10 sec | 25 min 10 sec | 13 min | >90 min |
| Storage Stability (day) | 30 | 15 | 4 | 16 | 28 | 51 | >60 |
| Storage Stability/Gelling Time (day/sec) | 0.0652 | 0.0073 | 0.0027 | 0.0291 | 0.0185 | 0.0654 | 0.0111 |

Ionic liquids H to W are the same as in Tables 7 and 8.

With the ionic liquids L, N and R with which the storability was relatively poor, the storage stability in these Examples was on a practicable level (longer than 10 days at 30° C.). Addition of triethyl borate also improved the storage stability with the ionic liquid P.

Examples 68 to 83

Using the ionic liquids H to W, they were tested for the effect of curing acceleration for polythiol and triethyl borate-comprising polythiol.

TABLE 11

| Material | Example 68 | Example 69 | Example 70 | Example 71 | Example 72 | Example 73 | Example 74 | Example 75 |
|---|---|---|---|---|---|---|---|---|
| Bisphenol A-type Epoxy Resin "EP828" | 100 | 100 | 100 | 100 | 100 | 100 | 100 | 100 |
| Ionic Liquid H | 0.35 | | | | | | | |
| Ionic Liquid I | | 0.44 | | | | | | |
| Ionic Liquid J | | | 0.29 | | | | | |
| Ionic Liquid K | | | | 0.33 | | | | |
| Ionic Liquid L | | | | | 0.31 | | | |
| Ionic Liquid M | | | | | | 0.41 | | |
| Ionic Liquid N | | | | | | | 0.43 | |
| Ionic Liquid O | | | | | | | | 0.43 |
| Polythiol "TMTP" | 59 | 59 | 59 | 59 | 59 | 59 | 59 | 59 |
| Triethyl Borate | 1.4 | 1.4 | 1.4 | 1.4 | 1.4 | 1.4 | 1.4 | 1.4 |
| Appearance of Adhesive | transparent | transparent | transparent | transparent | transparent | transparent | transparent | transparent |
| Gelling Time | 2 min 14 sec | 27 sec | 23 sec | 49 sec | 1 min 15 sec | 31 sec | 26 sec | 28 sec |
| Storage Stability (day) | 52 | 15 | 28 | 42 | 41 | 21 | 21 | 21 |
| Storage Stability/Gelling Time (day/sec) | 0.3881 | 0.5556 | 1.2174 | 0.8571 | 0.5467 | 0.6774 | 0.8077 | 0.7500 |

TABLE 12

| Material | Example 76 | Example 77 | Example 78 | Example 79 | Example 80 | Example 81 | Example 82 | Example 83 |
|---|---|---|---|---|---|---|---|---|
| Bisphenol A-type Epoxy Resin "EP828" | 100 | 100 | 100 | 100 | 100 | 100 | 100 | 100 |
| Ionic Liquid P | 0.44 | | | | | | | |
| Ionic Liquid Q | | 0.33 | | | | | | |
| Ionic Liquid R | | | 0.44 | | | | | |
| Ionic Liquid S | | | | 0.36 | | | | |
| Ionic Liquid T | | | | | 0.37 | | | |
| Ionic Liquid U | | | | | | 0.31 | | |
| Ionic Liquid V | | | | | | | 0.35 | |
| Ionic Liquid W | | | | | | | | 0.21 |
| Polythiol "TMTP" | 59 | 59 | 59 | 59 | 59 | 59 | 59 | 59 |
| Triethyl Borate | 1.4 | 1.4 | 1.4 | 1.4 | 1.4 | 1.4 | 1.4 | 1.4 |
| Appearance of Adhesive | transparent | transparent | transparent | transparent | transparent | transparent | transparent | transparent |
| Gelling Time | 32 sec | 11 min 17 sec | 30 sec | 27 sec | 30 sec | 35 sec | 30 sec | 11 min 50 sec |
| Storage Stability (day) | 21 | 50 | 22 | 25 | 10 | 22 | 35 | >60 |
| Storage Stability/Gelling Time (day/sec) | 0.6563 | 0.0739 | 0.7333 | 0.9259 | 0.3333 | 0.6286 | 1.1667 | 0.0845 |

(Notes)
Ionic liquids H to W are the same as in Tables 7 and 8.

All the ionic liquids investigated in the above were recognized to have an accelerating effect of curing. Even the ionic liquids having an extremely low reactivity as a curing agent could have an accelerating effect of curing on a practicable level for polythiol. Some ionic liquids were analyzed for the thermal curing reaction through differential scanning calorimetry (DSC), and it was confirmed that they showed extremely sharp endothermic reaction and the curing time with them was short, and that they were excellent in the degree of thermal curing reaction completion.

Examples 84 to 101

Using the ionic liquids A, D and H to W, epoxy resins comprising an acid anhydride, 4-methylhexahydrophthalic acid anhydride MH700-G (by New Japan Chemical), were tested to see whether inonic liquids function as curing accelerator.

TABLE 13

| Material | Example 84 | Example 85 | Example 86 | Example 87 | Example 88 | Example 89 | Example 90 | Example 91 | Example 92 |
|---|---|---|---|---|---|---|---|---|---|
| Bisphenol A-type Epoxy Resin "EP828" | 100 | 100 | 100 | 100 | 100 | 100 | 100 | 100 | 100 |
| Ionic Liquid A | 1 | | | | | | | | |
| Ionic Liquid D | | 1 | | | | | | | |

TABLE 13-continued

| Material | Example 84 | Example 85 | Example 86 | Example 87 | Example 88 | Example 89 | Example 90 | Example 91 | Example 92 |
|---|---|---|---|---|---|---|---|---|---|
| Ionic Liquid H | | | 1.6 | | | | | | |
| Ionic Liquid I | | | | 2 | | | | | |
| Ionic Liquid J | | | | | 1.3 | | | | |
| Ionic Liquid K | | | | | | 1.5 | | | |
| Ionic Liquid L | | | | | | | 1.5 | | |
| Ionic Liquid M | | | | | | | | 1.9 | |
| Ionic Liquid N | | | | | | | | | 2 |
| MH-700G | 80 | 80 | 80 | 80 | 80 | 80 | 80 | 80 | 80 |
| Appearance of Adhesive | transparent | transparent | transparent | transparent | transparent | transparent | transparent | transparent | transparent |
| Gelling Time | 3 min 28 sec | 3 min 8 sec | 1 min 55 sec | 2 min 35 sec | 2 min | 1 min 55 sec | 2 min 10 sec | 2 min 10 sec | 2 min |
| Storage Stability (day) | 3 | 2 | 2 | 2 | 2 | 2 | 2 | 2 | 2 |
| Storage Stability/Gelling Time (day/sec) | 0.0144 | 0.0106 | 0.0174 | 0.0129 | 0.0167 | 0.0174 | 0.0154 | 0.0154 | 0.0167 |

TABLE 14

| Material | Example 93 | Example 94 | Example 95 | Example 96 | Example 97 | Example 98 | Example 99 | Example 100 | Example 101 |
|---|---|---|---|---|---|---|---|---|---|
| Bisphenol A-type Epoxy Resin "EP828" | 100 | 100 | 100 | 100 | 100 | 100 | 100 | 100 | 100 |
| Ionic Liquid O | 2 | | | | | | | | |
| Ionic Liquid P | | 2 | | | | | | | |
| Ionic Liquid Q | | | 1.6 | | | | | | |
| Ionic Liquid R | | | | 2 | | | | | |
| Ionic Liquid S | | | | | 1.7 | | | | |
| Ionic Liquid T | | | | | | 1.7 | | | |
| Ionic Liquid U | | | | | | | 1.5 | | |
| Ionic Liquid V | | | | | | | | 1.6 | |
| Ionic Liquid W | | | | | | | | | 1 |
| MH-700G | 80 | 80 | 80 | 80 | 80 | 80 | 80 | 80 | 80 |
| Appearance of Adhesive | transparent | transparent | transparent | transparent | transparent | transparent | transparent | transparent | transparent |
| Gelling Time | 1 min 45 sec | 2 min 10 sec | 4 min 15 sec | 2 min 12 sec | 2 min | 2 min 20 sec | 2 min 20 sec | 3 min | >60 min |
| Storage Stability (day) | 2 | 1 | 3 | 3 | 3 | 2 | 2 | 2 | 7 |
| Storage Stability/Gelling Time (day/sec) | 0.0190 | 0.0077 | 0.0118 | 0.0227 | 0.0250 | 0.0143 | 0.0143 | 0.0111 | 0.0019 |

Ionic liquid A and ionic liquid D are the same as in Table 3; and ionic liquids H to W are the same as in Tables 7 and 8.

It was confirmed that the ionic liquids A, D and H to V are effective as a curing accelerator for acid anhydrides.

Examples 102 to 110

The newly synthesized ionic liquids (a) to (i) were used and investigated for the curability of epoxy resin. The results are shown below.

TABLE 15

| Material | Example 102 | Example 103 | Example 104 | Example 105 | Example 106 | Example 107 | Example 108 | Example 109 | Example 110 |
|---|---|---|---|---|---|---|---|---|---|
| Bisphenol A-type Epoxy Resin | 100 | 100 | 100 | 100 | 100 | 100 | 100 | 100 | 100 |
| Ionic Liquid a | 2.2 | | | | | | | | |
| Ionic Liquid b | | 3.4 | | | | | | | |
| Ionic Liquid c | | | 2.6 | | | | | | |
| Ionic Liquid d | | | | 2.1 | | | | | |
| Ionic Liquid e | | | | | 3.8 | | | | |
| Ionic Liquid f | | | | | | 3.1 | | | |

TABLE 15-continued

| Material | Example 102 | Example 103 | Example 104 | Example 105 | Example 106 | Example 107 | Example 108 | Example 109 | Example 110 |
|---|---|---|---|---|---|---|---|---|---|
| Ionic Liquid g | | | | | | | 2.4 | | |
| Ionic Liquid h | | | | | | | | 4 | |
| Ionic Liquid i | | | | | | | | | 3 |
| Appearance of Adhesive | semitransparent | semitransparent | semitransparent | semitransparent | semitransparent | semitransparent | semitransparent | transparent | semitransparent |
| Gelling Time | 30 sec | 2 min 50 sec | 1 min 30 sec | 35 sec | 2 min 15 sec | 2 min 30 sec | 2 min 2 sec | 1 min 50 sec | 1 min 50 sec |
| Storage Stability (day) | 6 | 37 | 24 | 20 | 41 | 35 | 34 | 22 | 43 |
| Storage Stability/Gelling Time (day/sec) | 0.2000 | 0.2176 | 0.2667 | 0.5714 | 0.3037 | 0.2333 | 0.2787 | 0.2000 | 0.3909 |

Ionic Liquid a: 1-ethyl-3-methylimidazolium acetate (Production Example 17).
Ionic Liquid b: 1-ethyl-1-methylpiperidinium (S)-(−)-2-pyrrolidone-5-carboxylate (Production Example 18).
Ionic Liquid c: 1-ethyl-3-methylimidazolium (L)-lactate (Production Example 19).
Ionic Liquid d: 1-ethyl-3-methylimidazolium formate (Production Example 20).
Ionic Liquid e: 1-ethyl-3-methylimidazolium hippurate (Production Example 21).
Ionic Liquid f: 1-ethyl-3-methylimidazolium (S)-(−)-2-pyrrolidone-5-carboxylate (Production Example 22).
Ionic Liquid g: bis(1-ethyl-3-methylimidazolium) L-tartrate (Production Example 23).
Ionic Liquid h: 1-ethyl-3-methylimidazolium N-benzoyl-DL-alaninate (Production Example 24).
Ionic Liquid i: 1-ethyl-3-methylimidazolium N-acetylglycinate (Production Example 25).

The results in Table 15 show that all the ionic liquids acted to cure epoxy resin. In particular, it is shown that the ionic liquid (i) and then the ionic liquid (e) and the ionic liquid (g) were good in the balance of the gelling time and the storage stability. However, the ionic liquid (d) showed the shortest gelling time, but at that temperature, the resin composition foamed.

Examples 111 to 119

The newly synthesized ionic liquids (a) to (i) were used and investigated for the curing speed and the storage stability of triethyl borate-comprising epoxy resin.

TABLE 16

| Material | Example 111 | Example 112 | Example 113 | Example 114 | Example 115 | Example 116 | Example 117 | Example 118 | Example 119 |
|---|---|---|---|---|---|---|---|---|---|
| Bisphenol A-type Epoxy Resin | 100 | 100 | 100 | 100 | 100 | 100 | 100 | 100 | 100 |
| Ionic Liquid a | 2.2 | | | | | | | | |
| Ionic Liquid b | | 3.4 | | | | | | | |
| Ionic Liquid c | | | 2.6 | | | | | | |
| Ionic Liquid d | | | | 2.1 | | | | | |
| Ionic Liquid e | | | | | 3.8 | | | | |
| Ionic Liquid f | | | | | | 3.1 | | | |
| Ionic Liquid g | | | | | | | 2.4 | | |
| Ionic Liquid h | | | | | | | | 4 | |
| Ionic Liquid i | | | | | | | | | 3 |
| Appearance of Adhesive | semitransparent | semitransparent | semitransparent | semitransparent | semitransparent | semitransparent | semitransparent | semitransparent | semitransparent |
| Gelling Time | 31 min 30 sec | 20 min 20 sec | 20 min 10 sec | 25 min 20 sec | 31 min 20 sec | 31 min 20 sec | 38 min 50 sec | 15 min | 25 min 50 sec |
| Storage Stability (day) | 21 | 42 | 42 | 42 | 52 | 42 | >60 | 43 | >60 |
| Storage Stability/Gelling Time | 0.0111 | 0.0344 | 0.0347 | 0.0276 | 0.0277 | 0.0222 | 0.0258 | 0.0478 | 0.0387 |

Ionic liquids (a) to (i) are the same as in Table 15.

The results in Table 16 show that triethyl borate added to the resin compositions comprising any of the ionic liquid (a) to the ionic liquid (i) improved the storage stability of the compositions, and in particular, the composition with the ionic liquid (a) having poor storage stability was greatly improved.

Examples 120 to 128

Using the newly synthesized ionic liquids (a) to (i), they were tested for the effect of curing acceleration for polythiol and triethyl borate-comprising polythiol.

TABLE 17

| Material | Example 120 | Example 121 | Example 122 | Example 123 | Example 124 | Example 125 | Example 126 | Example 127 | Example 128 |
|---|---|---|---|---|---|---|---|---|---|
| Bisphenol A-type Epoxy Resin "EP828" | 100 | 100 | 100 | 100 | 100 | 100 | 100 | 100 | 100 |
| Ionic Liquid a | 0.16 | | | | | | | | |
| Ionic Liquid b | | 0.24 | | | | | | | |
| Ionic Liquid c | | | 0.19 | | | | | | |
| Ionic Liquid d | | | | 0.15 | | | | | |
| Ionic Liquid e | | | | | 0.27 | | | | |
| Ionic Liquid f | | | | | | 0.23 | | | |
| Ionic Liquid g | | | | | | | 0.17 | | |
| Ionic Liquid h | | | | | | | | 0.29 | |
| Ionic Liquid i | | | | | | | | | 0.21 |
| Polythiol "TMTP" | 59 | 59 | 59 | 59 | 59 | 59 | 59 | 59 | 59 |
| Triethyl Borate | 1.4 | 1.4 | 1.4 | 1.4 | 1.4 | 1.4 | 1.4 | 1.4 | 1.4 |
| Appearance of Adhesive | transparent | transparent | transparent | transparent | transparent | transparent | transparent | transparent | transparent |
| Gelling Time | 1 min 10 sec | 55 sec | 1 min 40 sec | 1 min 10 sec | 1 min 15 sec | 1 min 15 sec | 5 min 30 sec | 1 min 15 sec | 1 min 30 sec |
| Storage Stability (day) | >60 | 57 | >60 | >60 | 57 | 57 | >60 | 57 | >60 |
| Storage Stability/Gelling Time (day/sec) | 0.8571 | 1.0364 | 0.6000 | 0.8571 | 0.7600 | 0.7600 | 0.1818 | 0.7600 | 0.6667 |

Ionic liquids (a) to (i) are the same as in Table 15.

As shown in Table 17, it was confirmed that all the ionic liquids (a) to (i) function as a curing accelerator for a polythiol, and as a whole, they give rapid-curable compositions having good storage stability, and in particular, the ionic liquid (b) secured the most rapid curability and was favorable.

Examples 129 to 137

Using the newly synthesized ionic liquids (a) to (i), epoxy resins comprising an acid anhydride, 4-methylhexahydrophthalic acid anhydride MH700-G (by New Japan Chemical), were tested for the curing effect.

TABLE 18

| Material | Example 129 | Example 130 | Example 131 | Example 132 | Example 133 | Example 134 | Example 135 | Example 136 | Example 137 |
|---|---|---|---|---|---|---|---|---|---|
| Bisphenol A-type Epoxy Resin "EP828" | 100 | 100 | 100 | 100 | 100 | 100 | 100 | 100 | 100 |
| Ionic Liquid a | 0.75 | | | | | | | | |
| Ionic Liquid b | | 1.12 | | | | | | | |
| Ionic Liquid c | | | 0.88 | | | | | | |
| Ionic Liquid d | | | | 0.68 | | | | | |
| Ionic Liquid e | | | | | 1.27 | | | | |
| Ionic Liquid f | | | | | | 1.05 | | | |
| Ionic Liquid g | | | | | | | 0.81 | | |
| Ionic Liquid h | | | | | | | | 1.33 | |
| Ionic Liquid i | | | | | | | | | 1 |
| MH-700G | 80 | 80 | 80 | 80 | 80 | 80 | 80 | 80 | 80 |
| Appearance of Adhesive | transparent | transparent | transparent | transparent | transparent | transparent | transparent | transparent | transparent |
| Gelling Time | 3 min 20 sec | 3 min | 3 min 15 sec | 3 min 45 sec | 3 min 35 sec | 3 min 20 sec | 3 min 40 sec | 3 min 35 sec | 3 in 15 sec |
| Storage Stability (day) | 4 | 6 | 6 | 4 | 6 | 6 | 6 | 6 | 6 |
| Storage Stability/Gelling Time (day/sec) | 0.0200 | 0.0333 | 0.0308 | 0.0178 | 0.0279 | 0.0300 | 0.0273 | 0.0279 | 0.0308 |

Ionic liquids (a) to (i) are the same as in Table 15.

As shown in Table 18, it was confirmed that the ionic liquids (a) to (i) function as a curing accelerator for an acid anhydride. As a whole, it was confirmed that these ionic liquids prolonged the storage stability by from 2 to 3 times, as compared with the ionic liquid A, the ionic liquid D and the ionic liquids H to V shown in Table 13 and Table 14.

Production Example 26

At 0° C., 4.2 g of (S)-(-)-2-pyrrolidone-5-carboxylic acid (by Wako Pure Chemical Industry) was added to 21.3 g of tetrabutylphosphonium hydroxide (aqueous 41.4% solution, by Hokko Chemical), and stirred for 10 minutes. Using an evaporator, the pressure was reduced to 40 to 50 mmHg, and this was concentrated at 60 to 80° C. for 2 hours, and then at 90° C. for 3 hours. Thus, 13.3 g of tetrabutylphosphonium (S)-(-)-2-pyrrolidone-5-carboxylate (purity: 94.1%) was obtained as an oily compound. The obtained ionic liquid had the same properties as in Production Example 1.

Production Example 27

At 0° C., 3.54 g of N-acetylglycinate (by Tokyo Chemical) was added to 20.0 g of tetrabutylphosphonium hydroxide (aqueous 41.4% solution, by Hokko Chemical), and stirred for 10 minutes. Using an evaporator, the pressure was reduced to 40 to 50 mmHg, and this was concentrated at 60 to 80° C. for 2 hours, and then at 90° C. for 5 hours. At room temperature, this was again dissolved in 14.2 ml of ethyl acetate (Junsei Chemical). Using an evaporator, the pressure was reduced to 40 to 50 mmHg, and this was concentrated at 70 to 90° C. for 3 hours. Thus, 11.7 g of tetrabutylphosphonium N-acetylglycinate (purity: 96.9%) was obtained as an oily compound. The obtained ionic liquid had the same properties as in Production Example 16.

NMR spectrum:
$^1$HNMR (CDCl$_3$) δ: 0.89-0.99 (m, 12H), 1.42-1.55 (m, 16H), 1.92 (s, 3H), 2.24-2.35 (m, 8H), 3.66 (d, J=3.8 Hz, 2H), 6.70 (br s, 1H).

Formulation Example 1

An adhesive having a composition mentioned below was prepared. It was confirmed that this is a completely-liquid one-component adhesive having both good narrow adhesiveness and good impregnation adhesiveness.

| | |
|---|---|
| Ingredient (1): 20%-episulfidized bisphenol A-type epoxy resin, "YL7150" (trade name by Japan Epoxy Resin) | 100 parts by weight |
| Ingredient (2): Ionic liquid A (tetrabutylphosphonium (S)-(-)-2-pyrrolidone-5-carboxylate (Production Example 1) | 5 parts by weight |

Industrial Applicability

According to the present invention, there are provided a practicable resin composition comprising constitutive elements of readily available materials and having well-balanced suitable curing capability and storage stability, and further fine chemical products such as adhesives, casting agents, sealing agents, sealants, fiber-reinforcing resins, coating agents or paints; and accordingly, the invention is meaningful in the industrial fields of electric and electronic parts and automobiles. In particular, in case where an ambient temperature ionic liquid is used, the invention may provide a completely-liquid one-component resin composition having excellent operability and suitable for application to narrow-gap adhesion and impregnation adhesion, and is therefore extremely meaningful.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A resin composition comprising:
 (a) at least one compound selected from the group consisting of:
  (a1) a compound which contains at least two epoxy groups in the molecule;
  (a2) a compound which contains at least two thiirane groups in the molecule; and
  (a3) a compound which contains at least one epoxy group and at least one thiirane group in the molecule; and
 (b) at least one ionic liquid wherein said ionic liquid is selected from the group consisting of tetrabutylphosphonium (S)-(-)-2-pyrrolidone-5-carboxylate, tetrabutylphosphonium decanoate, N-methyl-N-propylpiperidinium bis(trifluoromethanesulfonyl)imidate, N-methyl-N-propylpyrrolidinium bis(trifluoromethanesulfonyl)imidate, tetrabutylphosphonium trifluoroacetate, tetrabutylphosphonium α-lipoate, tetrabutylphosphonium (L)-lactate, bis(tetrabutylphosphonium) L-tartrate, tetrabutylphosphonium hippurate, tetrabutylphosphonium N-methylhippurate, tetrabutylphosphonium benzoyl-DL-alaninate, tetrabutylphosphonium N-acetyl-L-phenylalaninate, tetrabutylphosphonium methanesulfonate, tetrabutylphosphonium 2,6-di-tert-butylphenol, tetrabutylphosphonium L-aspartate, tetrabutylphosphonium glycinate, tetrabutylphosphonium N-acetylglycinate, 1-ethyl-1-methylpiperidinium (S)-(-)-2-pyrrolidone-5-carboxylate, 1-ethyl-3-methylimidazolium hippurate, 1-ethyl-3-methylimidazolium (S)-(-)-2-pyrrolidone-5-carboxylate, bis(1-ethyl-3-methylimidazolium) L-tartrate, 1-ethyl-3-methylimidazolium N-benzoyl-DL-alaninate, 1-ethyl-3-methylimidazolium N-acetylglycinate.

2. The resin composition as claimed in claim 1, which further comprises:
 (c) at least one polythiol compound having at least two thiol groups in the molecule.

3. A cured product, which is obtained by curing a resin composition as claimed in claim 2.

4. The resin composition as claimed in claim 1, which further comprises:
 (d) at least one compound having Lewis acidity.

5. A cured product, which is obtained by curing a resin composition as claimed in claim 4.

6. The resin composition as claimed in claim 1, which further comprises:
 (e) at least one acid anhydride.

7. A cured product, which is obtained by curing a resin composition as claimed in claim 6.

8. A fine chemical product, comprising a resin composition as claimed in claim 1.

9. The fine chemical product as claimed in claim 8, which is an adhesive, a casting agent, a sealing agent, a sealant, a fiber-reinforcing resin, a coating agent, or a paint.

10. A cured product, which is obtained by curing a resin composition as claimed in claim 1.

11. A resin composition comprising:
(a) at least one compound selected from the group consisting of:
  (a1) a compound which contains at least two epoxy groups in the molecule;
  (a2) a compound which contains at least two thiirane groups in the molecule; and
  (a3) a compound which contains at least one epoxy group and at least one thiirane group in the molecule; and
(b) at least one ionic liquid wherein said ionic liquid is selected from tetrabutylphosphonium (S)-(-)-2-pyrrolidone-5-carboxylate, tetrabutylphosphonium decanoate, tetrabutylphosphonium (L)-lactate, tetrabutylphosphonium hippurate, tetrabutylphosphonium N-methylhippurate, tetrabutylphosphonium benzoyl-DL-alaninate, tetrabutylphosphonium N-acetyl-L-phenylalaninate, tetrabutylphosphonium 2,6-di-tert-butylphenol, tetrabutylphosphonium glycinate, tetrabutylphosphonium N-acetylglycinate, 1-ethyl-1-methylpiperidinium (S)-(-)-2-pyrrolidone-5-carboxylate, 1-ethyl-3-methylimidazolium hippurate, 1-ethyl-3-methylimidazolium (S)-(-)-2-pyrrolidone-5-carboxylate, 1-ethyl-3-methylimidazolium N-benzoyl-DL-alaninate, 1-ethyl-3-methylimidazolium N-acetylglycinate;
(c) at least one polythiol compound having at least two thiol groups in the molecule.

12. The resin composition as claimed in claim 11, which further comprises:
(d) at least one compound having Lewis acidity.

13. A cured product, which is obtained by curing a resin composition as claimed in claim 11.

14. A cured product, which is obtained by curing a resin composition as claimed in claim 12.

15. The resin composition as claimed in claim 11, which further comprises:
(e) at least one acid anhydride.

16. A cured product, which is obtained by curing a resin composition as claimed in claim 15.

17. A fine chemical product, comprising a resin composition as claimed in claim 11.

18. The fine chemical product as claimed in claim 17, which is an adhesive, a casting agent, a sealing agent, a sealant, a fiber-reinforcing resin, a coating agent, or a paint.

19. A cured product, which is obtained by curing a resin composition as claimed in claim 17.

20. A resin composition comprising:
(a) at least one compound selected from the group consisting of:
  (a1) a compound which contains at least two epoxy groups in the molecule;
  (a2) a compound which contains at least two thiirane groups in the molecule; and
  (a3) a compound which contains at least one epoxy group and at least one thiirane group in the molecule; and
(b) at least one ionic liquid wherein said ionic liquid is selected from
  tetrabutylphosphonium (S)-(-)-2-pyrrolidone-5-carboxylate, tetrabutylphosphonium decanoate, tetrabutylphosphonium (L)-lactate, tetrabutylphosphonium hippurate, tetrabutylphosphonium N-methylhippurate, tetrabutylphosphonium benzoyl-DL-alaninate, tetrabutylphosphonium N-acetyl-L-phenylalaninate, tetrabutylphosphonium N-acetylglycinate, 1-ethyl-3-methylimidazolium N-benzoyl-DL-alaninate, 1-ethyl-3-methylimidazolium N-acetylglycinate
(d) at least one compound having Lewis acidity.

21. The resin composition as claimed in claim 20, which further comprises:
(c) at least one polythiol compound having at least two thiol groups in the molecule.

22. A cured product, which is obtained by curing a resin composition as claimed in claim 21.

23. The resin composition as claimed in claim 20, which further comprises:
(e) at least one acid anhydride.

24. A cured product, which is obtained by curing a resin composition as claimed in claim 23.

25. A fine chemical product, comprising a resin composition as claimed in claim 20.

26. The fine chemical product as claimed in claim 25, which is an adhesive, a casting agent, a sealing agent, a sealant, a fiber-reinforcing resin, a coating agent, or a paint.

27. A cured product, which is obtained by curing a resin composition as claimed in claim 25.

28. A cured product, which is obtained by curing a resin composition as claimed in claim 20.

29. A resin composition comprising:
(a) at least one compound selected from the group consisting of:
  (a1) a compound which contains at least two epoxy groups in the molecule;
  (a2) a compound which contains at least two thiirane groups in the molecule; and
  (a3) a compound which contains at least one epoxy group and at least one thiirane group in the molecule; and
(b) 1-ethyl-1-methylpiperidinium (S)-(-)-2-pyrrolidone-5-carboxylate
(e) at least one acid anhydride.

30. The resin composition as claimed in claim 29, which further comprises:
(c) at least one polythiol compound having at least two thiol groups in the molecule.

31. The resin composition as claimed in claim 29, which further comprises:
(d) at least one compound having Lewis acidity.

32. A fine chemical product, comprising a resin composition as claimed in claim 29.

33. The fine chemical product as claimed in claim 32, which is an adhesive, a casting agent, a sealing agent, a sealant, a fiber-reinforcing resin, a coating agent, or a paint.

34. A cured product, which is obtained by curing a resin composition as claimed in claim 29.

35. A cured product, which is obtained by curing a resin composition as claimed in claim 30.

36. A cured product, which is obtained by curing a resin composition as claimed in claim 31.

37. A cured product, which is obtained by curing a resin composition as claimed in claim 32.

* * * * *